US010827953B2

(12) United States Patent
Rabinovitz et al.

(10) Patent No.: US 10,827,953 B2
(45) Date of Patent: Nov. 10, 2020

(54) DEVICES, SYSTEMS AND METHODS FOR IN-VIVO IMMUNOASSAY

(71) Applicant: GIVEN IMAGING LTD., Yoqneam (IL)

(72) Inventors: Elisha Rabinovitz, Haifa (IL); Osnat Sella-Tavor, Kfar Kish (IL); Amit Pascal, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 190 days.

(21) Appl. No.: 15/578,505

(22) PCT Filed: Jun. 2, 2016

(86) PCT No.: PCT/IL2016/050571
§ 371 (c)(1),
(2) Date: Nov. 30, 2017

(87) PCT Pub. No.: WO2016/193981
PCT Pub. Date: Dec. 8, 2016

(65) Prior Publication Data
US 2018/0160950 A1 Jun. 14, 2018

Related U.S. Application Data

(60) Provisional application No. 62/169,701, filed on Jun. 2, 2015.

(51) Int. Cl.
*A61B 5/1455* (2006.01)
*A61B 5/07* (2006.01)
(Continued)

(52) U.S. Cl.
CPC ............ *A61B 5/14507* (2013.01); *A61B 5/01* (2013.01); *A61B 5/05* (2013.01); *A61B 5/073* (2013.01);
(Continued)

(58) Field of Classification Search
None
See application file for complete search history.

(56) References Cited

U.S. PATENT DOCUMENTS

2006/0149143 A1 7/2006 Colvin
2008/0064923 A1 3/2008 Rabinovitz et al.
(Continued)

FOREIGN PATENT DOCUMENTS

CN 103827668 A 5/2014
EP 2689729 1/2014

*Primary Examiner* — Eric F. Winakur
*Assistant Examiner* — Marjan Fardanesh
(74) *Attorney, Agent, or Firm* — Pearl Cohen Zedek Latzer Baratz LLP

(57) ABSTRACT

A swallowable in-vivo device comprising a shell formed with at least one inlet extending across a shell wall and configured for allowing ingress of fluid at least into the shell; the shell accommodates therein a lateral flow (LF) arrangement configured for absorbing the fluid; the LF arrangement comprises a test zone configured for coming into contact, in-vivo, with a predetermined N substance present in the fluid or a compound comprising the substance, thereby causing a change in at least one property of the test zone; the shell further accommodates a sensor configured for sensing, in-vivo, the at least one property, at least when changed by interaction with the fluid; the LF arrangement has at least one curved segment, and at least one exposure portion juxtaposed with the inlet, configured for absorbing the fluid passing through the inlet into the shell.

23 Claims, 19 Drawing Sheets

(51) Int. Cl.
    *A61B 5/00*     (2006.01)
    *A61B 5/145*     (2006.01)
    *G01N 33/558*     (2006.01)
    *A61B 5/01*     (2006.01)
    *A61B 5/05*     (2006.01)
    *A61B 5/1486*     (2006.01)

(52) U.S. Cl.
    CPC ...... *A61B 5/14503* (2013.01); *A61B 5/14539* (2013.01); *A61B 5/14546* (2013.01); *A61B 5/14865* (2013.01); *A61B 5/6861* (2013.01); *G01N 33/558* (2013.01); *A61B 5/4216* (2013.01); *A61B 2562/0295* (2013.01); *A61B 2562/162* (2013.01); *A61B 2562/166* (2013.01)

(56) References Cited

U.S. PATENT DOCUMENTS

| | | |
|---|---|---|
| 2008/0284599 A1 | 11/2008 | Zdeblick et al. |
| 2008/0306359 A1 | 12/2008 | Zdeblick et al. |
| 2011/0257490 A1 | 10/2011 | Semler |
| 2013/0289368 A1 | 10/2013 | Covington et al. |
| 2014/0206956 A1 | 7/2014 | Rabinovitz et al. |

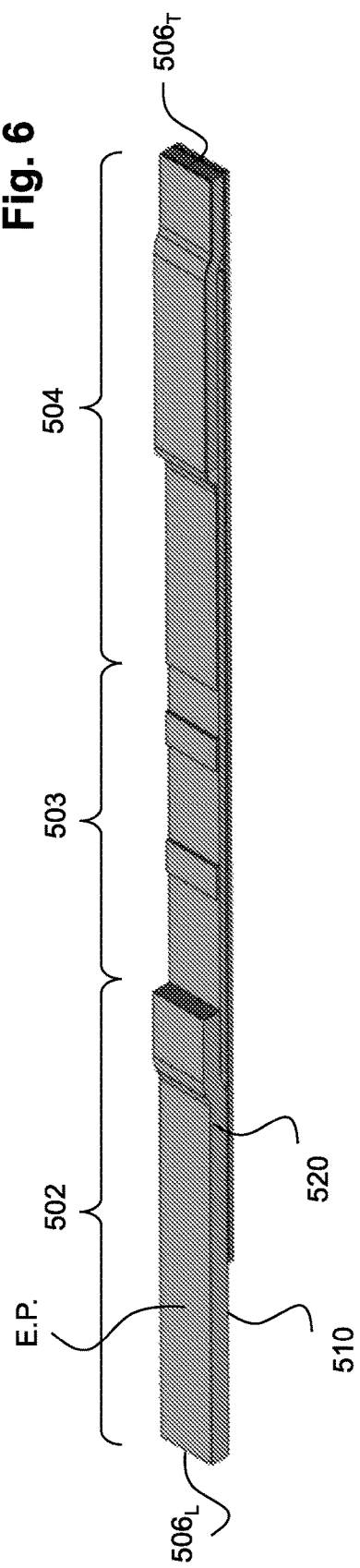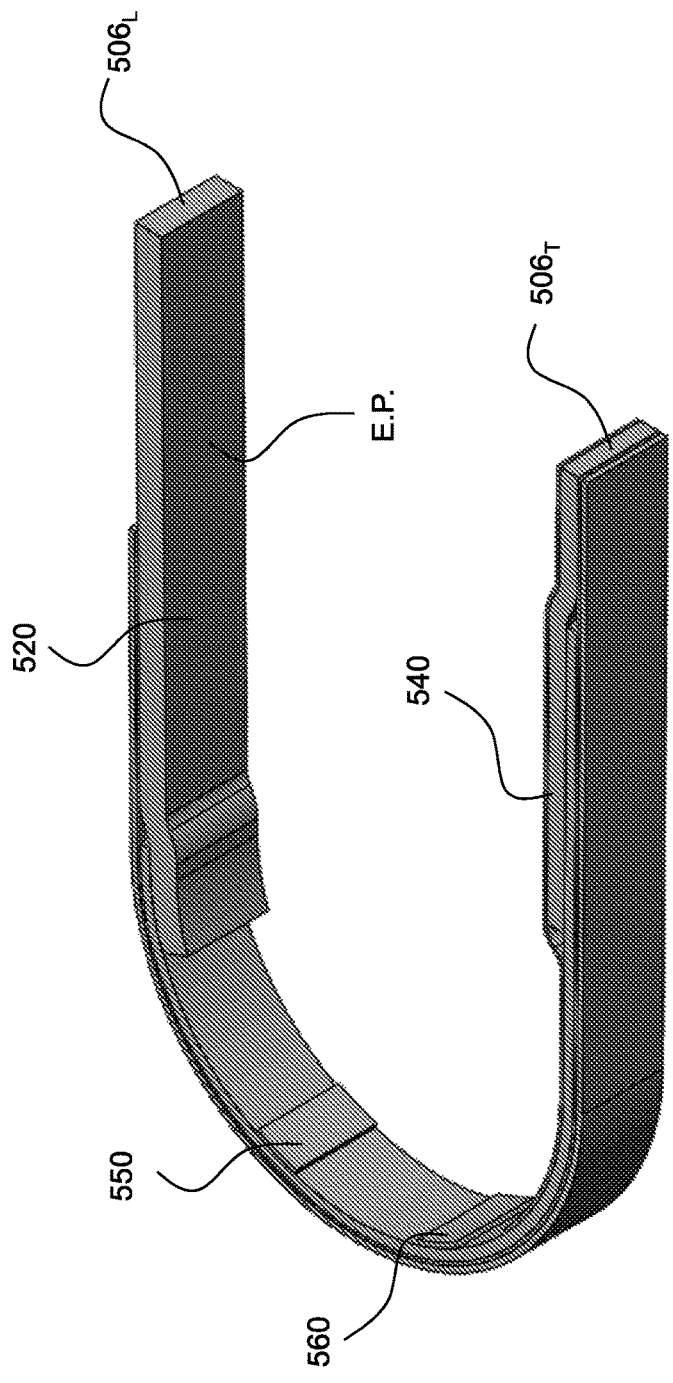

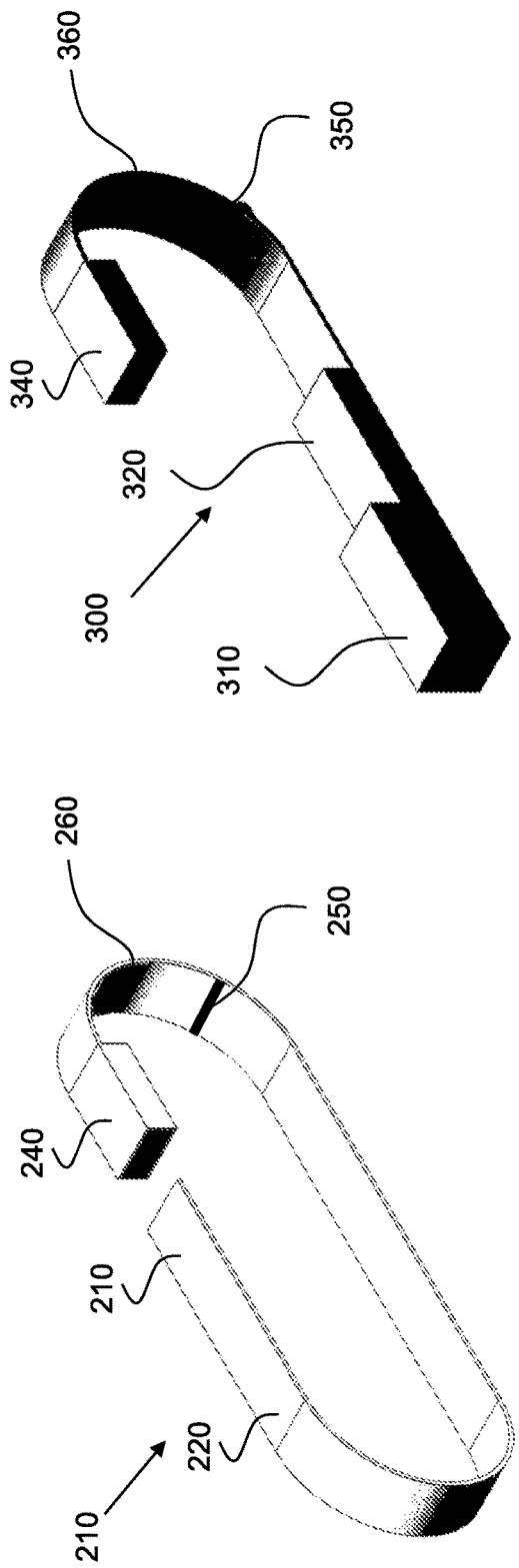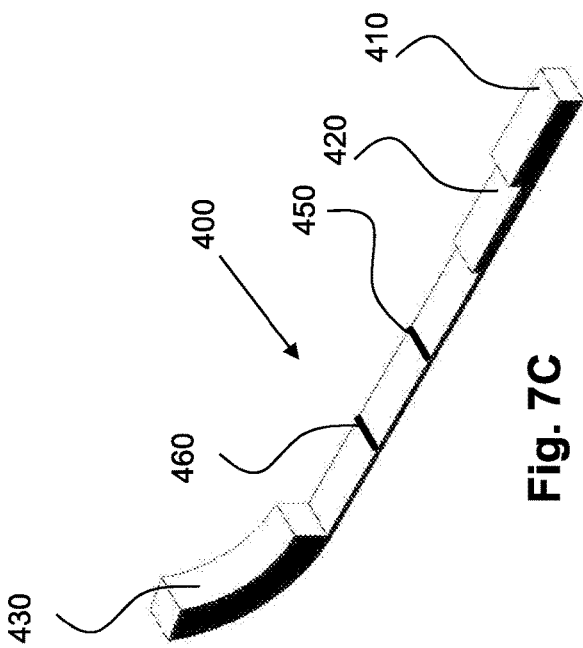
Fig. 7A
Fig. 7B
Fig. 7C

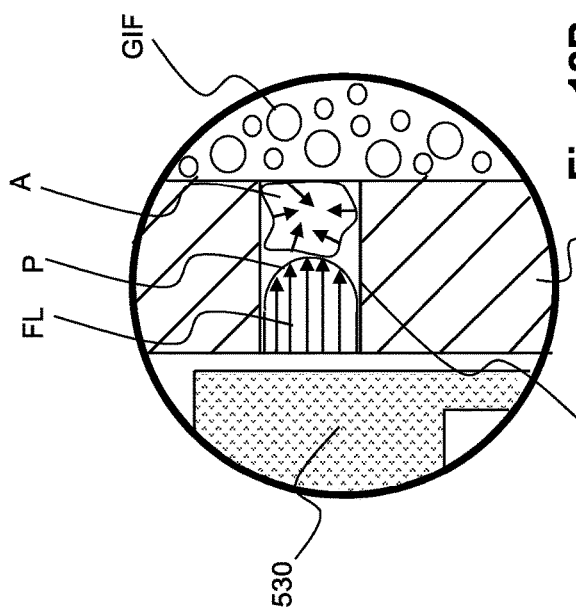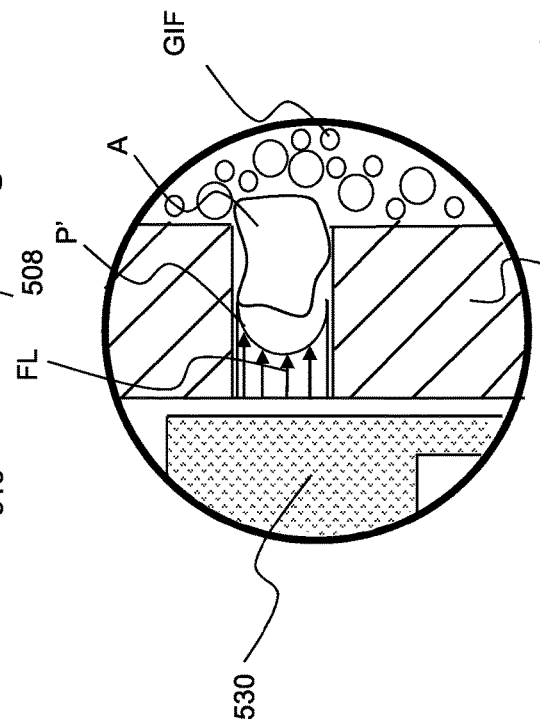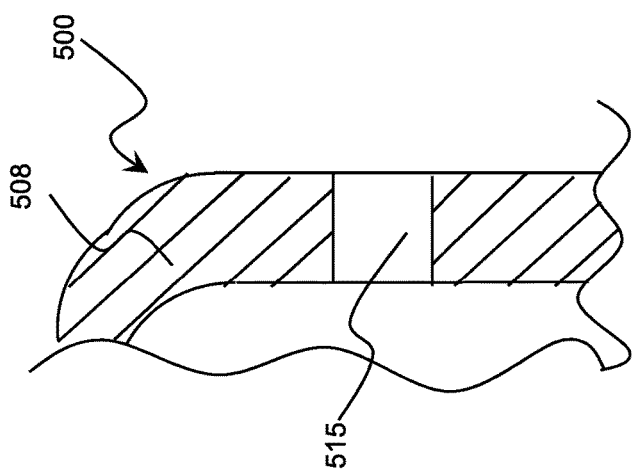

DEVICES, SYSTEMS AND METHODS FOR IN-VIVO IMMUNOASSAY

PRIOR APPLICATION DATA

This application is a U.S. National Stage of International Application No. PCT/IL2016/050571, International Filing Date Jun. 2, 2016, claiming benefit of U.S. Provisional Application No. 62/169,701, filed Jun. 2, 2015, which is incorporated by reference.

TECHNOLOGICAL FIELD

The present invention relates to in vivo immunoassay in general, and to immunoassay using swallowable capsules in particular.

BACKGROUND OF THE INVENTION

The basic principle of any immunochemical technique is that a specific antibody is combined with a specific antigen to give an exclusive antibody-antigen complex. Antigens are generally of high molecular weight and commonly are proteins or polysaccharides. Polypeptides, lipids, nucleic acids and many other materials can also function as antigens. Immune responses may also be generated against smaller substances, called haptens, if these are chemically coupled to a carrier protein or other synthetic matrices. A variety of molecules such as drugs, simple sugars, amino acids, small peptides, phospholipids, or triglycerides may function as haptens. Thus, assuming time is of no issue, about any foreign substance can be identified by the immune system and evoke specific antibody production.

Immunoassays are rapid, sensitive, and selective, and are generally cost effective. They have been applied to clinical diagnostics, environmental analysis and food safety assessment. Many types of immunoassay have been used to detect the presence of various substances, often generally called ligands, in body fluids such as blood and urine. Such assays involve antigen-antibody reactions, synthetic conjugates comprising radioactive, enzymatic, fluorescent, or visually observable metal sol tags, and specially designed reactor chambers. In these assays, there is a receptor, e.g., an antibody, which is specific for the selected ligand or antigen, and a means for detecting the presence, and often the amount, of the ligand-receptor reaction product. Most current tests are designed to make a quantitative determination, but in many cases all that is required is a positive/negative indication. For these tests, visually observable indicia such as the presence of agglutination or a color change are preferred.

Lateral flow immunoassay, which is also known as the immuno-chromatographic assay, or "strip" test, is an example of a widespread test that is simple to perform by almost anyone and operates more rapidly than traditional laboratory-based testing. This area of diagnostics has grown dramatically in recent years, with the most common and well-known of these being the home pregnancy test.

The principle of a lateral flow immunoassay relies on the competition for binding sites on polymer or metal particles. Antibodies that are raised to a specific target are bound to metal nanoparticles or dyed polymer particles. These particles are then applied using an immersion procedure onto a release pad (a sample pad) in order to produce a stable particle reservoir for release onto a nitrocellulose-based membrane. Two lines of reagents are immobilized onto, or formed or built into, the nitrocellulose-based membrane: a target reference, or test line, comprising a conjugate that can specifically bind the target to be identified, and (followed by) a spaced apart control line that is a line of anti-species antibody. The sample pad and membrane are assembled together with an absorbent pad. The sample is initially added to the adsorbent pad and the strip is left for a few minutes after which the result is visually read directly, looking for the coloration of the lines. This technology is ideally suited for rapid diagnostics.

Most medical detection kits utilizing the lateral flow immunoassay are based on in-vitro testing of body fluid, such as urine or blood. For example, in some cases, diseases, such as cancer, are detected by analyzing the blood stream for tumor specific markers, typically specific antibodies.

Another example is the presence of elevated concentrations of red blood cells in the gastrointestinal (GI) tract that may indicate different pathologies, depending on the location of the bleeding along the GI tract. Thus, for instance, bleeding in the stomach may indicate an ulcer, whereas bleeding in the small intestine may indicate the presence of a tumor. Furthermore, different organs may contain different body fluids requiring different analysis methods. For example, the stomach secretes acids, whereas pancreatic juice is basic.

Thus, early in-vivo detection, identification and location of abnormal conditions (such as, for example, an atypical presence or concentration of a substance in body fluids) may be critical for definitive diagnosis and/or treating of various pathologies.

It is, therefore, an object of the present invention to provide a swallowable in-vivo device with on-board chromatographic strip that can provide rapid and sensitive in-vivo detection of low levels of various ligands, antigens or antibodies in body fluids. Another object of the present invention is to provide a swallowable in-vivo device with a chromatographic strip that is adapted to detect low levels of various ligands, antigens or antibodies in body fluids at various sites/locations in the GI tract.

FIG. 1 (prior art) shows an example chromatography strip 100. Chromatography strip (lateral flow strip—"LFS") 100 typically includes a sample (absorbent) pad 11 to which the body lumen liquid sample may be applied, a conjugate (reagent) pad 12 that may contain antibodies specific to the target analyte molecules (ligands or antigens) and that may be conjugated to colored particles, such as colloidal metal (e.g., gold) particles or polymer (e.g., latex) microspheres, a reaction membrane 13 (e.g., a hydrophobic nitrocellulose or cellulose acetate membrane) onto which anti-target analyte antibodies are immobilized in a test line 16 and a control line 17 (a control line may contain either antigens or antibodies specific to the conjugate antibodies), and a waste (reservoir) 14, which is an absorbent pad designed to draw the sample fluid(s) across the reaction membrane 13 by capillary action and collect it. The LFS's elements described above may be fixed to an inert backing material 15 that may be from, for example, plastic.

Essential in the lateral flow immunoassay is the movement of a liquid sample, or its extract containing the analyte of interest along the chromatography strip, thereby passing various areas of the strip where binding molecules have been attached that exert more or less specific interactions with the analyte.

Sample pad 11 is usually made of cellulose, glass fiber, cross-linked silica or other material where body fluid sample can initially be drawn from the exterior body lumen and then subjected to the lateral flow immunoassay. If necessary, sample pad 11 may optionally modify the sample to improve the results of the assay. This might be by modifying pH, filtering out solid components, separating whole body fluid constituents, adsorbing out unwanted particles and compounds or some other test specific variable. For some applications, the sample pad may be pre-treated by being dipped into a specific buffer containing a mix of a solution comprised of soluble proteins, surfactants, detergents and other polymers. Such buffer allows for a steady lateral flow and prevents nonspecific binding of sample components to the pad.

In close contact with plastic backing 15 and sample pad 11 is conjugate (reagent) pad 12, which is usually made of cross-linked silica. A colored reagent, such as a detection labeled conjugate, is dried down and held in place on this pad.

After absorbing the drawn body liquid onto sample pad 11, the liquid moves into conjugate pad 12 by capillary action, re-hydrates the labelled conjugate particles and allows the mixing of these particles with the absorbed body liquid. The labelled conjugate interacts with the specific analyte contained in the drawn body liquid flow, thereby initiating the intermolecular interactions, which are dependent on the affinity and avidity of the reagents. These interactions will continue during the entire chromatographic separation process.

The labels may be prepared of colored or fluorescent nanoparticles for optical detection. In principle, any colored particles can be used. However, commonly, either latex (blue color) or nanometer sized particles of gold (red color) are used. The gold particles are red in color due to localized surface plasmon resonance. Fluorescent or magnetic labelled particles can also be used; however, these require the use of an electronic reader to assess the test result.

The size of the labels (nanoparticles) are in the order of nanometers to allow unobstructed flow through the membrane. The labels may be selenium particles, carbon macrocycles or liposomes, besides the aforementioned colloidal gold and latex particles. In liposomes colored, fluorescent or bioluminescent dyes can be incorporated, allowing visualization, and, when applicable, quantification of the response. The newest labels may also include quantum dots.

As mentioned above, conjugate pad 12 is usually made of cross-linked silica, but it may also be made from non-absorbent material such as fiberglass, polyester, rayon or a similar material. The conjugate pad is preferably comprised of a synthetic material (at least when using a gold conjugate) to ensure the efficient release of its contents. Pre-treatment of the conjugate pad helps to ensure that the conjugate releases at the proper rate and enhances its stability. The pre-treatment is performed in the same way as with the sample pad.

The complex of the labelled conjugate and analyte then moves into reaction membrane 13. The membrane 13 may be produced from nitrocellulose, nylon, polyethersulfone, polyethylene or fused silica.

The nitrocellulose membrane consists of a very thin Mylar sheet coated with a layer of nitrocellulose (NC). The benefits of using NC as an immunoassay matrix include low cost, good capillary flow, high binding affinity for protein, ease of handling and cutting, as well as the ability of manufactures to varying thickness and components of the membrane in order to suit the specific application. The NC membrane binds proteins electrostatically through an interaction with the nitrate esters and the peptide bonds of the protein.

As shown on FIG. 1, at least two lines are sprayed on the strip: a test line 16 and a control line 17, which have both been pre-treated with specific antibodies or antigens (ligands), and which is the standard for lateral flow immunoassays. These lines are usually closer to the wicking pad 14 than to the conjugate pad 12 in order to improve the overall performance of the lateral flow immunoassay. Some lateral flow assays may have more than one test line, but each additional test line greatly increases the complexity of development, and thus increases cost.

Initially, the complex of the labelled conjugate and analyte moves onto the membrane 13. Then it starts migrating towards the test line 16 capturing and recognizing the binding analyte, where it becomes immobilized and produces a distinct signal for example, in the form of a colored line, indicating the test is complete. A distinct signal at control line 17 may indicate a proper flow of the body liquid through chromatography strip 3. Depending upon the analytes present in the body liquid and on the type of the immunoassay performed, the colored reagent can become bound at the test line 16 and at the control line 17, or, alternatively, only at the control line 17.

The so called "wick" (wicking or waste) pad 14 maintains a lateral flow along the chromatography strip. Wick pad 14 may be made from non-woven, cellulose fiber sheets. These pads can be manufactured in a variety of thicknesses and densities to suit the needs of the immunoassay.

There are different types of the lateral flow immunoassay available on the market. For example, in the double antibody sandwich immunoassay, the drawn body fluid migrates from sample pad 11 through conjugate pad 12 where any target analyte present will bind to the labelled conjugate particles. The sample fluid mixture then continues to migrate across the membrane until it reaches the test line 16, where the target/conjugate complex binds to the immobilized antibodies, producing a visible line on membrane 13. The fluid then migrates further along the strip until it reaches the control line 17, where excess conjugate binds and produces a second visible line on the membrane. Control line 17 is therefore indicative of the sample that has migrated across membrane 13 as intended. Thus, two colored lines 16 and 17 appearing on membrane 13 is a positive result. A single colored control line 17 is a negative result. Double antibody sandwich assays are most suitable for larger analytes, such as bacterial pathogens and viruses, with multiple antigenic sites.

Competitive assays are primarily used for testing small molecules and differ from the double antibody sandwich immunoassay in that the conjugate pad contains antibodies that are already bound to the target analyte or to an analogue thereof. If the target analyte is present in the sample, it will therefore not bind with the conjugate and will remain unlabelled. As the sample migrates along reaction membrane 13 and reaches test line 16, an excess of unlabelled analyte will bind to the immobilized antibodies and block the capture of the conjugate, so that no visible line is produced. The unbound conjugate will then bind to the antibodies in control line 17, producing a colored line. The single colored control line 17 on the reaction membrane 13 is a positive result. Two colored lines 16 and 17 is a negative result. However, if an excess of unlabelled target analyte is not present, a weak line may be produced in the test line 16, indicating an inconclusive result. Competitive assays are most suitable for testing for small molecules, such as mycotoxins, unable to bind to more than one antibody simultaneously.

There are a number of variations on a lateral flow immunoassay technology. Test line 16 on membrane 13 may contain immobilized antigens or enzymes (depending on the target analyte) rather than antibodies. In this case, as above, two colored lines 16 and 17 indicate a negative result, whereas one single colored control line shows a positive result. In a slightly modified format, the competitive immunoassay may be also used for detection of specific antibodies in the body fluid. It is also possible to apply multiple test lines to create a multiplex immunoassay.

Lateral flow immunoassays are simple to use by untrained operators and generally produce a result within several minutes. The lines 16 and 17 can take as little as a few minutes to develop. Generally, there is a tradeoff between time and sensitivity, such that more sensitive tests may take longer to develop. The lateral flow immunoassays typically require little or no sample or reagent preparation. They are very stable and robust, have a long shelf life and do not usually require refrigeration. They are also relatively inexpensive to produce. These features make them ideal for use in the in vivo diagnostic device according to the embodiments of the invention Acknowledgement of the above references herein is not to be inferred as meaning that these are in any way relevant to the patentability of the presently disclosed subject matter.

SUMMARY

In accordance with a general aspect of the subject matter of the present application, there is provided a miniaturized LFS modified for being contained in a swallowable capsule (e.g., Pillcam® of Given Imaging Ltd.) and able to draw-in body fluids and provide useful biological-related measurements while in the gastrointestinal (GI) tract.

In accordance with one aspect of the subject matter of the present application there is provided a swallowable in-vivo device comprising:
  a shell formed with at least one inlet extending across a shell wall between an inner surface and outer surface thereof, and configured for allowing ingress of fluid at least into said shell, said shell accommodating therein:
  a lateral flow (LF) arrangement configured for absorbing said fluid, said LF arrangement comprising a test zone configured for coming into contact, in-vivo, with a predetermined substance present in said fluid or a compound comprising said substance, thereby causing a change in at least one property of said test zone;
  a sensor configured for sensing, in-vivo, said at least one property, at least when changed by interaction with said fluid;
  wherein said LF arrangement is positioned within the shell such that it has at least one curved segment, and at least one exposure portion juxtaposed with said at least one inlet, configured for absorbing at least some of said fluid passing through said at least one inlet into the shell.

The shell may comprise a main body extending along a longitudinal axis of the shell and a first end and a second end located on axially opposite sides of said main body, and wherein said curved segment extends transverse to said longitudinal axis. The shell may also be constructed such that at least one of its ends is curved and wherein the curvature of said curved segment corresponds to that of said end.

For example, the in-vivo device can comprise a shell (208), a first dome (209/1) on a first end of the shell and a second dome (209/2) on a second end of the shell. The domes (e.g., 209/1, 209/2) may lying on a longitudinal axis (201) of the shell (208). A closed gate (e.g., 202, 1250) may be configured to open in a predetermined location in the GI tract to enable GI/body fluid(s) to enter the in-vivo device (e.g., 200, 800 and 900).

Under the above example, the LF arrangement further comprises a second, longitudinal segment extending generally along the longitudinal axis. Specifically, the second, longitudinal segment can extend along the shell and is spaced from the longitudinal axis. According to a specific example, the second, longitudinal segment can include at least a part of said exposure portion.

In accordance with a specific design embodiment, the LF arrangement may comprises:
  a first section comprising a sample zone and a conjugate zone;
  a second section comprising said test zone; and
  a third section comprising an absorbent zone.

Specifically, the in-vivo device can comprise a lateral flow strip structure (e.g., 210, 300, 400, 500, 600, 1100) to absorb GI fluids entering the in-vivo device through the gate. The LFS may include a test section (e.g., 214, 340, 440, 570, 602, 922) to interact, in vivo, with a substance or particles included in the GI fluid. The LFS structure may include one or more straight segments spaced away from, and parallel to, the longitudinal axis (e.g., 201) of the in-vivo device, and one or more curved segments, where the curved segment(s) may have a curvature that conforms to a curvature of the dome(s). The swallowable in-vivo device may also include a sensor (e.g., imagers 850, 950) to sense, in vivo, a property of the substance or particles in the fluid(s) in response to the interaction.

In accordance with one example, the LFS may be specifically configured for characterization and quantification of small molecules and protein biomarkers of GI diseases. Examples of such biomarkers may include, but are not limited to at least any one of the following: calprotectin, lactoferrin, albumin, hemoglobin, CEA, CA19-9, CA 72-4, LYVE-1, REG1A, TFF1 and ammonia. The concentration of the biomarkers in the collected fluids from different parts of the GI can determined by quantitative assays—such as ELISA or lateral flow immunoassay or mass spectrometry. Concentration will be determined in mg/ml.

The property of the test zone which is sensed by the sensing system can include, but is not limited to, at least any one of the following: color, pH level, electric conductivity and magnetic properties.

In particular, the test section of a LFS may include, among other things, a cellulose membrane, a test line (e.g., test line 260, 360, 450, 550, 818, 918) and a control line (e.g., control line 270, 350, 460, 560, 820, 920). The lateral flow strip may include a sample pad, a conjugate pad, a cellulose membrane including a test line and a control line, and an absorbent pad. One or more of the sample pad, conjugate pad, cellulose membrane and absorbent pad may be mounted on, or form, the straight segment of the LFS. One or more of the sample pad, conjugate pad, cellulose membrane and absorbent pad may be mounted on, or form, the curved segment of the LFS.

Under the above example, any one of the following arrangements is applicable:
  the exposure portion may include at least a part of said sample zone;
  the curved segment may include at least a part of said second section;
  the curved segment may include least a portion of said test zone.

The second section of the LF arrangement may be made of a cellulose membrane having formed thereon a test line and a control line.

According to a particular example, the LF arrangement may comprise a lateral flow strip (LFS). In particular, said LFS may extend along at least a periphery of the shell.

Specifically, said LFS may have a first end and a second and, said curved segment being delimited by a lead end and a trail end, and wherein the LFS may assume any one of the following configurations when accommodated within the shell:
said lead end constitutes the first end of the LFS and said trail end constitutes the second end of the LFS;
said lead end constitutes the first end of the LFS and said trail end is spaced from the second end of the LFS;
said lead end is spaced from the first end of the LFS and said trail end constitutes the second end of the LFS; and
each of the lead end and the trail end are spaced from each of the first end and second end of the LFS.

The LFS may be U-shaped so that it has a first end segment including the first end of the LFS and a second end segment including the second end of the LFS, each of the end segments extending generally along the longitudinal axis of the in-vivo device.

The LFS may also comprise a backing layer extending along at least a portion of said curved segment. It is noted that fluid is configured for propagating through the LFS via capillary channels formed therein, wherein deforming (e.g. bending, folding, creasing etc.) of the LFS may damage the integrity of the capillary channels, thereby impeding progression of fluid along the strip. The presence of the backing layer elegantly solves this problem by preventing such damage to the capillary channels at the curved segment of the strip.

It is appreciated that the configuration of the LF arrangement within the in-vivo device of the present application is not limited to a U-shape and may also assume at least any one of the following configurations: a 1-curved strip structure (FIG. 3), a 2-curved strip structure (FIG. 2), a semi-curved strip structure (FIG. 4), "U"-shaped strip structure (FIG. 5) and an all-straight-line strip structure (FIG. 6).

In accordance with one example, the LF arrangement may be constituted by a single LFS. In accordance with another example, the LF arrangement can comprise two or more LFSs. Under this example, each of the two or more LFSs defines a virtual plane including the longitudinal axis of the in-vivo device, at least two of such virtual planes being angled to one another about the longitudinal axis. The virtual planes of said two or more LFSs may be equally angularly spaced with respect to each other.

For example, the LFS structure may include one LFS, or N LFSs (e.g., N=2, N=3, etc.). The N LFSs may respectively lay on, form or represent N planes, and each two adjacent planes of the N planes may be angularly displaced 360/N degrees.

The in-vivo device may further comprise a gate arrangement juxtaposed with said at least one inlet, and configured for:
remaining naturally closed, thereby restricting ingress of fluid into said shell through said at least one inlet; and
opening at least in a predetermined location along the gastrointestinal tract to enable fluid to enter said shell through said at least one inlet to come into contact with said at least one exposure portion.

Under an example in which the LF arrangement comprises two or more LFSs, the in-vivo device may comprise two or more gate arrangements, each being associated with a different LFS.

The gate may be configured to open under predetermined conditions commensurate to a desired location along the GI tract, thereby exposing said at least one inlet. Such conditions may be any one of the following types: time dependent conditions, pH dependent conditions, enzymatic environment conditions, prevailing bacteria conditions, temperature conditions and prevailing electromagnetic field conditions.

In accordance with a particular example, the in-vivo device may comprise a first inlet covered by a first gate arrangement and a second inlet covered by a second gate arrangement. Specifically, the first gate arrangement may be configured to open under a first set of conditions while the second gate may be configured to open under a second set of conditions different than the first set of conditions.

The gate arrangement may assume any of the following design configurations:
the gate arrangement comprises a closure which is biodegradable and/or dissolvable, subject to the above predetermined conditions, to expose said inlet. In this case, the closure can be a thin film layer which may be adhered to the shell;
the gate arrangement comprises a closure secured to the shell by a component which is biodegradable and/or dissolvable, subject to the above predetermined conditions, to thereby disengage the closure from the shell and expose said inlet. In this case, the closure may be a plug and said component may be a biodegradable O-ring.

When the closure is a plug, it may comprise an electrode which may be configured, when the closure is properly positioned with respect to the inlet, for closing an electrical circuit in the in-vivo device, thereby indicating that the inlet is properly sealed.

For example, the plug may include an electrode (e.g., 1010) that, in conjunction with electrodes (e.g., 1020) of the in-vivo device may close an electrical circuit in the in-vivo device to indicate to a controller (e.g., 1040) that the plug is in place, sealing the gate.

In case there are N LFSs, the in-vivo device may include N gates, a gate for each lateral flow strip, and each gate may be sealed by a plug. Different plugs may be designed to biodegrade/dissolve in different GI locations. Some plugs may be designed to biodegrade/dissolve in a same GI location.

The sensor of the in-vivo device may be configured for sensing at least any one of the following parameters: light, pH, electrical charge, chemical substances and temperature. In case the sensed parameter is light, the sensor may be constituted by an imaging device.

In accordance with a different arrangements, the cellulose membrane including the test line and the control line may be located/mounted adjacent to the shell (FIG. 8, a 'side' view configuration), or adjacent to the dome (FIG. 9, a 'front' view configuration).

It should be appreciated that while the in-vivo is configured for identifying and determining a change in the property of said LF arrangement owing to its interaction with the GI fluid, it may also be configured for sensing additional parameters not associated with the LF arrangement. For example, the in-vivo device may comprise a sensor arrangement comprising a first sensor configured for sensing a change in the property of the LF arrangement, and a second sensor configured for sensing other parameter/s. For example, the sensing arrangement can comprise an imaging device configured for obtaining an image of the GI tract.

In accordance with a particular example, the sensing arrangement can be a single imaging device having a field of view (F.O.V) which includes both the LF arrangement and an area external to the F.O.V.

The in-vivo device may also comprise:
- a printed circuit board (PCB; e.g., 830, 930A, 930B) on which the sensor and other electrical components are mounted; and
- a separation wall forming a physical barrier (LFS-PCB separation wall, e.g., 1270) between the LF arrangement and the PCB to prevent fluids absorbed by the LF arrangement from reaching the PCB.

The in-vivo device may also comprise a fluid redirecting member (FRM; e.g., 1212) configured for directing fluid emitted from the LF arrangement into the shell back to the LF arrangement. The fluid redirecting member (FRM) may be placed at an entrance of a parasitic channel (e.g., 1290) formed between the LF arrangement and said separation wall.

The shell of the in-vivo device may also be formed with at least one outlet extending across a shell wall between an inner surface and outer surface thereof, said outlet being configured for allowing egress of fluid out of said shell. Specifically, the outlet may be configured for allowing air contained in said shell and/or in said LF arrangement to escape said shell as the LF arrangement gradually absorbs fluid while preventing fluid from entering said shell therethrough.

It is appreciated that in its initial state (i.e. before the gate is opened and fluid is absorbed by the LF arrangement), the capillaries of the LFS are filled with air. As a result, when the gate is opened and fluid from an environment external to the shell begins seeping through these capillaries, the propagation of the fluid pushes out that air, along the capillaries.

Thus, the in-vivo device may be designed in at least one of the following two configurations addressing this phenomenon:
- retaining the air within the shell (i.e. not letting it escape) involving a certain increase in the internal pressure present in the shell; and
- utilizing an outlet configured for allowing air to gradually escape as fluid gradually fills the capillary channels.

In particular, under a configuration in which an outlet is utilized, it is noted that different fluids exhibit different flow regimes and/or flow profiles and/or flow patterns when propagating within capillary channels. These differences may affect the pressure exerted on the air contained within the capillaries by the propagating fluid. It is also noted that since the in-vivo device is immersed in fluid (e.g. GI fluid), said fluid may have a given surface tension over an external opening of said outlet.

Thus, under one flow regime, the pressure exerted on the air may be sufficient for overcoming the surface tension, thereby forcing air out of the shell while under another flow regime, the pressure exerted on the air may not be sufficient for overcoming the surface tension, whereby air does not escape the shell. However, in the latter case, it is required that the flow regime is sufficient for pressurizing the air of the capillaries, otherwise fluid may not be able to seep into and be absorbed by the LF arrangement. It should also be noted that since fluid it configured to flow within the LFS in a predetermined direction, it is required to prevent fluid from entering the shell via the outlet.

The outlet of the subject matter of the present application elegantly addresses the above mentioned issues by functioning as a smart valve—allowing air escape under a one flow regime, and allowing it to compress under another flow regime.

Specifically, the outlet may have a tapering shape so that it extends between an inner opening formed on an inner surface of the shell and having a first diameter $D1$, and an outer opening formed on the outer surface of the shell and having a second diameter $D2 \neq D1$. In particular, a surprising effect was achieved when the arrangement is so that $D1<D2$, preventing fluid from entering the shell.

At least one of the above openings may have a nominal diameter in any of the following ranges:
- 0.1 mm to 0.8 mm;
- 0.25 mm to 0.7 mm; and
- 0.4 mm to 0.6 mm.

Noting that the in-vivo device implements a curved LFS, the arrangement may be such that said LF arrangement has a nominal length $L$, and wherein said at least one inlet and said at least one outlet are located on said shell such that the distance between them is smaller than $L$. In accordance with a particular example, the distance between said at least one inlet and said at least one outlet is smaller than the distance between opposite ends of the in-vivo device measured along the longitudinal axis.

In accordance with another aspect of the subject matter of the present application, there is provided a swallowable in-vivo device comprising a shell formed with at least one inlet extending across a shell wall between an inner surface and outer surface thereof, and configured for allowing ingress of fluid at least into said shell, and with at least one outlet extending across a shell wall between an inner surface and outer surface thereof, and configured for allowing egress of fluid out of said shell; said shell accommodating therein:
- a lateral flow (LF) arrangement of length $L$, said LF arrangement being configured for absorbing at least some of said fluid;
- a sensor configured for sensing, in-vivo, a change in at least one property of said test zone as a result of absorbing said fluid by the latter;

wherein said at least one inlet and said at least one outlet are positioned on the shell such that the distance therebetween is smaller than $L$.

BRIEF DESCRIPTION OF THE DRAWINGS

In order to better understand the subject matter that is disclosed herein and to exemplify how it may be carried out in practice, the following embodiments will now be described, by way of non-limiting example only, with the intent that these examples not be restrictive. It will be appreciated that for simplicity and clarity of the illustration, elements shown in the figures referenced below may be shown schematically (e.g. not drawn to scale), and, where considered appropriate, reference numerals may be repeated among the figures to indicate like, corresponding or analogous elements.

FIG. 5B is a schematic isometric view of the LFS shown in FIG. 5A;

FIG. 6 is a schematic side view of an LFS shown in FIGS. 5A and 5B, shown in its original, straightened form;

FIGS. 7A, 7B and 7C are schematic isometric views of LFSs which may be used in the in-vivo devices shown in FIG. 2;

FIG. 12A is a schematic cross-section view of a shell wall of the in-vivo device according to an embodiment of the present invention;

FIGS. 12B and 12C are schematic enlarged views of a portion of the shell wall shown in FIG. 12A, illustrating two different flow regimes across an outlet in the shell;

DETAILED DESCRIPTION OF EMBODIMENTS

The description that follows provides various details of exemplary embodiments. However, this description is not intended to limit the scope of the claims but instead to explain various principles of the invention and the manner of practicing it.

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well-known features may be omitted or simplified in order not to obscure the invention.

The in-vivo diagnostic device of an embodiment of the invention may typically be fully autonomous and typically self-contained. For example, a device may be a capsule or other unit where all the components are substantially contained within a housing, case or shell, and where the device does not require wires or cables in order to receive power or transmit information, for example.

The in vivo device may be floatable or have a neutral or near neutral buoyancy in water or in other liquids that may fill body lumens (e.g., GI fluids). Accordingly, the device may have a specific gravity of 1.0 gr/cc or about 1.0 gr/cc. The in vivo device according to an embodiment may be designed to access pathologic lesions in nearly every region of the GI tract, including the colon, small bowel and biliary tree. The in-vivo device may be designed to collect samples for diagnosing pathological areas only and to bypass, or ignore, healthy sections/areas of the GI tract.

Figure 1:
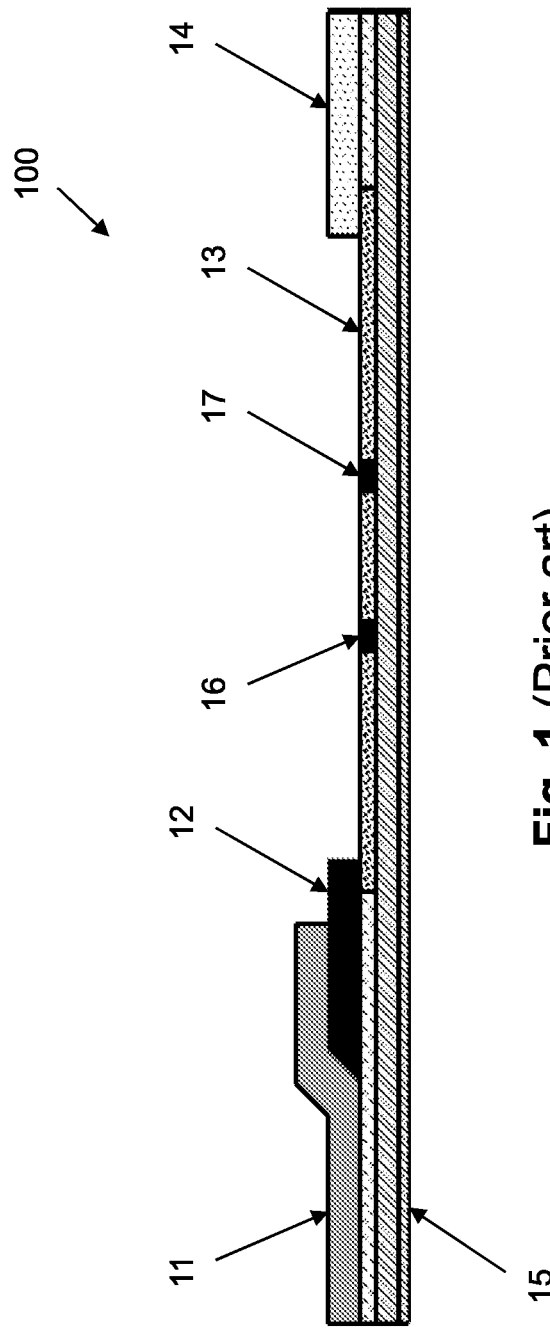
FIG. 1 (prior art) is a schematic cross-section view of a typical chromatography strip (LFS) used in the lateral flow immunoassay.
Figure 2:
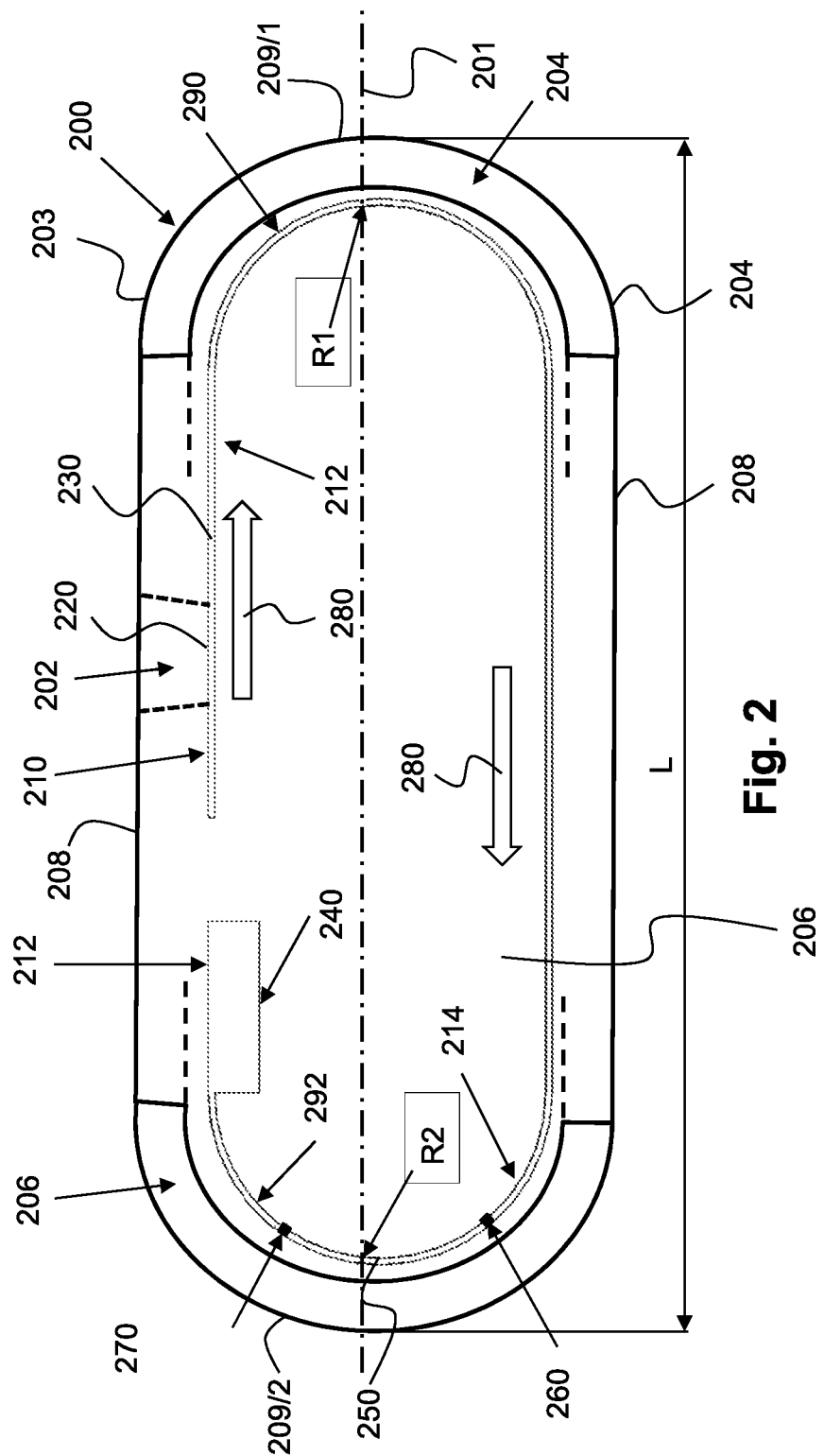
FIG. 2 is a schematic cross-section view of one example of an in-vivo device according to an embodiment of the present invention, having one LFS with two arched segments.

FIG. 2 schematically illustrates a four-curved lateral flow strip (LFS) according to an example embodiment. In-vivo device (e.g., capsule type) 200 includes a four curved LFS 210, and a controllable inlet opening (gate or port) 202 through which body fluids (e.g., fluids from different parts of the GI tract) can access, or be withdrawn to, LFS 210. In the LFS configuration shown in FIG. 2 LFS 210 includes two, mutually subtended, or opposite, curved sections or segments 290 and 290.

(Capsule 200 is shown in FIG. 2 including only LFS 210 for simplicity, and without a plug that seals gate 202 and is controllably releasable from the gate.) LFS 210 may include a sample pad 220 for absorbing fluid through gate 202, a conjugate pad 230 for 'tying' (conjugating) metal (e.g., gold) particles, used as marker, to (with) particles of the fluid, and an absorbent pad 240 that functions as a reservoir, to collect (through absorbing) excessive fluid. LFS 210 also includes a cellulose-based membrane 250 that may include a test line 260 and a spaced apart control line 270. Four-curved LST 210 has a configuration in which the sample pad (220), conjugated pad (230) and absorbent pad (240) lie on/in or are part of, or form, a straight line (212), and the cellulose section (214) with its 'on-board' test line (260) and control line (270), which constitutes the sensing part of LFS 210, lie on/in or are part of, or form, a curved line or curvilinear line 214.

Assuming capsule 200 is near a location of interest in the GI tract; for example near a damaged mucosa of the small bowel, a plug (not shown in FIG. 2) sealing gate 202 may controllably be removed to enable body fluid in the location of interest to enter capsule 200 through gate 202. Sampling pad 220, through capillary action, may start absorbing the fluid and, at some point, transfer it to conjugate pad 230 in order for conjugate pad 230 to bio-mark particles of the fluid by binding them to gold particles that are stored in conjugate pad 230. The fluid, continuing to move under capillary force in direction 280, may reach cellulose section (214), first to test line 260, then to control line 270. Test line 260, serving as a 'trap', may immobilize fluid particles to which gold particles are attached, to thereby enable to determine the presence of the fluid particles sought for by determining the presence of the gold particles. If the fluid does not contain the sought for fluid particles, test line 260 maintains its original/initial color. However, the same result may be due to improper, faulty or lack of movement of the tested fluid in LFS 210. Therefore, there is a need to ascertain proper movement of the fluid in LFS 210, and this is done by using also control line 270, which serves as a trap for the gold particles. A monitoring system (e.g., imaging system or a similar system) may be used to monitor the state or condition (e.g., electrical, chemical, optical or color condition, etc.) of test line 260 and control line 270 to enable, for example an on-board processor, to determine whether the sought for fluid particles are present in the tested fluid, or not.

Absorbent pad 240 has a limited capacity to accumulate/store fluid. When absorbent pad 240 reaches its designed storage limit, movement of the fluid along LFS 210 essentially stops. This physical property can be used as follows. Reading the state or condition of test line 260 and control line 270 (visually or otherwise; e.g., electrically) while fluid moves in LFS 210 may result in unsteady readings due to unsteady condition of the biochemical interaction of the lines with the fluid. Therefore, readings of the test line and control line should preferably be performing when the fluid in LFS 210 stops moving. The time elapsing from the time when the sample pad (220) is first exposed to the external fluid (through controllable gate or through opening 202) to the time when absorbent pad 240 reaches its designed storage limit depends on the overall length of LFS 210, and on the dimensions and materials of each part or component/section of LFS 210. Absorbent pad 240 may be designed such that sufficient fluid can flow and fill LFS 210 to its full length before the fluid stops moving in direction 280. Absorbent pad 240 may be designed to enable a predetermined time to elapse before the fluid stops its lengthwise movement in and/or along LFS 210.

The shell, case or housing of capsule 200 may have two opposite domes 204 and 206. LFS 210 may have two curved sections 290 and 292 (one curved section at or in each dome). The curvature of section 290 may be adjacent to dome 204 and conform to the curvature of dome 204. The curvature of section 292 may be adjacent to dome 206 and conform to the curvature of dome 206. The radius R1 of curved section 290 of LFS 210 may be five millimeters. The radius R2 of curved section 292 of LFS 210 may also be five millimeters (mm). (R1 and R2 may have other values and they may have different values, depending, for example, on space constraints within in-vivo device 200.) The thickness of absorbent pad 240 may be 1 mm or less than 1 mm (e.g., 0.85 mm), and the thickness of the other sections of, or forming, LFS 210 may be, for example, less than 0.5 mm (e.g., 0.45 mm). The length (L) of in-vivo device 200 may be 30 mm, or about 30 mm LFS 210 may have a width in the range of, for example, 3 mm-5 mm (Other width ranges may be used.)

Figure 3:
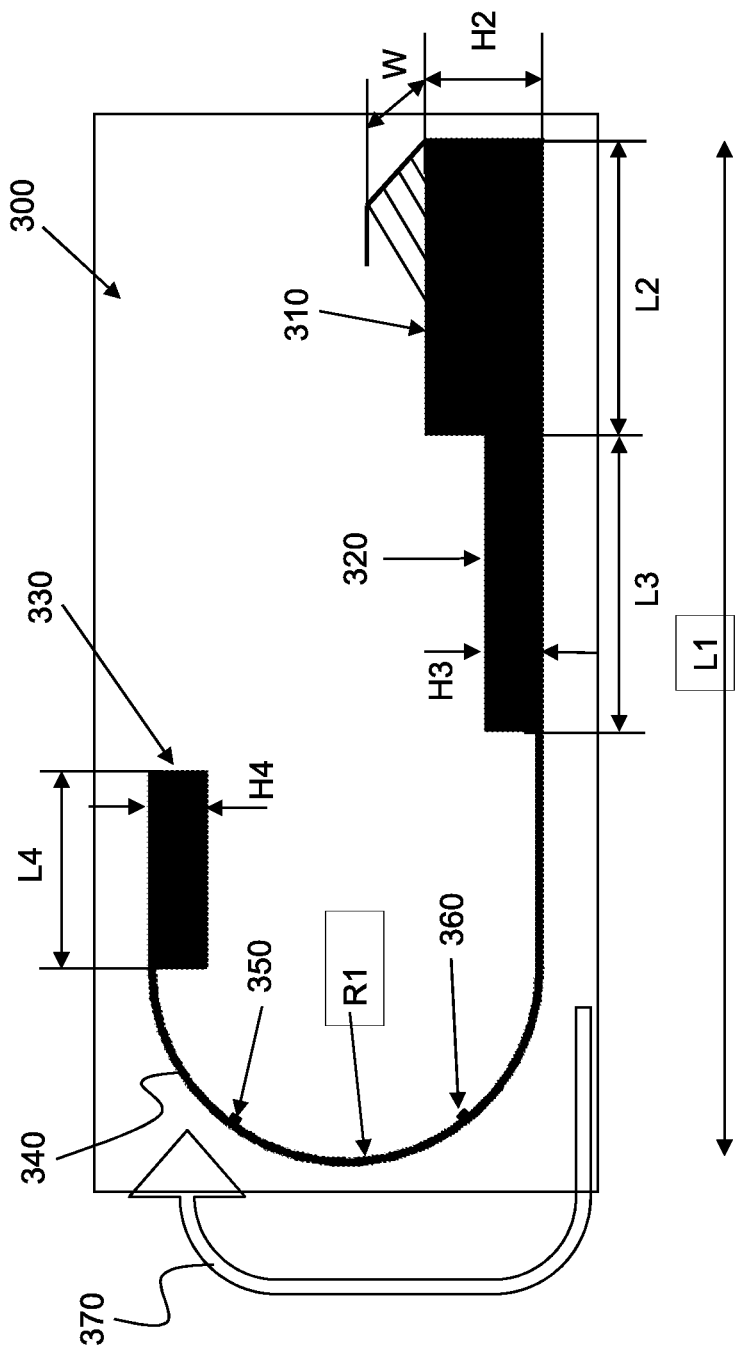
FIG. 3 is a schematic cross-section view of an example of an arched LFS, which may be used in-vivo device according to an embodiment of the present invention.

FIG. 3 schematically illustrates a two-curved, or one arched (half-capsule compliant), LFS according to another example embodiment. LFS 300 may include a sample pad 310, a conjugate pad 320 and an absorbent pad 330. Between conjugate pad 320 and absorbent pad 330 is located or interposed a cellulose-based membrane 340. Cellulose-based membrane 340 may include a test line 350 and a control line 360. The overall length (L1) of LFS 300 in its operational state (i.e., when it resides in the in-vivo device it is designed for; e.g., in capsule 200), may be, for example 25 mm, or about 25 mm (e.g., 25 mm±3 mm). The lengths L2 of sample pad 310, length L3 of conjugate pad 320 and length L4 of absorbent pad 330 may each have a value in the range of 3 mm-10 mm, for example. (Other length ranges may be used.) By way of example, sample pad 310 may be 4 mm long, conjugate pad 320 may be 3.5 mm long, and absorbent pad 330 may be 8 mm.

The thickness H2 of sample pad 310, thickness H3 of conjugate pad 320 and thickness H4 of absorbent pad 330 may each have a value in the range of 0.5 mm-10 mm, for example. (Other thickness ranges may be used.) By way of example, sample pad 310 may have a thickness H2 that is greater than the thickness H3 of conjugate pad 320. Absorbent pad 330 may have a thickness H4 that is greater, the same as or less than the thickness of conjugate pad 320. Absorbent pad 330 may have a thickness that is greater, the same as or less than the thickness of sample pad 310. By way of example, sample pad 310 may be 1 mm thick, conjugate pad 320 may be 0.45 mm thick, and absorbent pad 330 may be 6 mm thick. LFS 300 may have a width (W) in the range of, for example, 3 mm-5 mm (Other width ranges may be used.)

In operation, when a capsule containing LFS 300 reaches a designated site in the GI tract, a gate configured to open at that particular site is controllably opened (for example by dissolving a bio-dissolvable plug or a bio-dissolvable ring restraining a plug) to enable body fluids to reach sample pad 310. Sample pad 310 may start absorbing some of the body fluids, and, after a while, fluids absorbed by sample pad 310 may continue to lengthwise move, through capillary force, in direction 370, into and along conjugate pad 320, and from conjugate pad 320 to curved cellulose membrane 340, and from the curved cellulose membrane to absorbent pad 330, where fluids can accumulate up to the maximum fluid capacity designed for absorbent pad 330 according to, for example, the type(s) of fluids expected to be found at the particular GI site.

Figure 4:
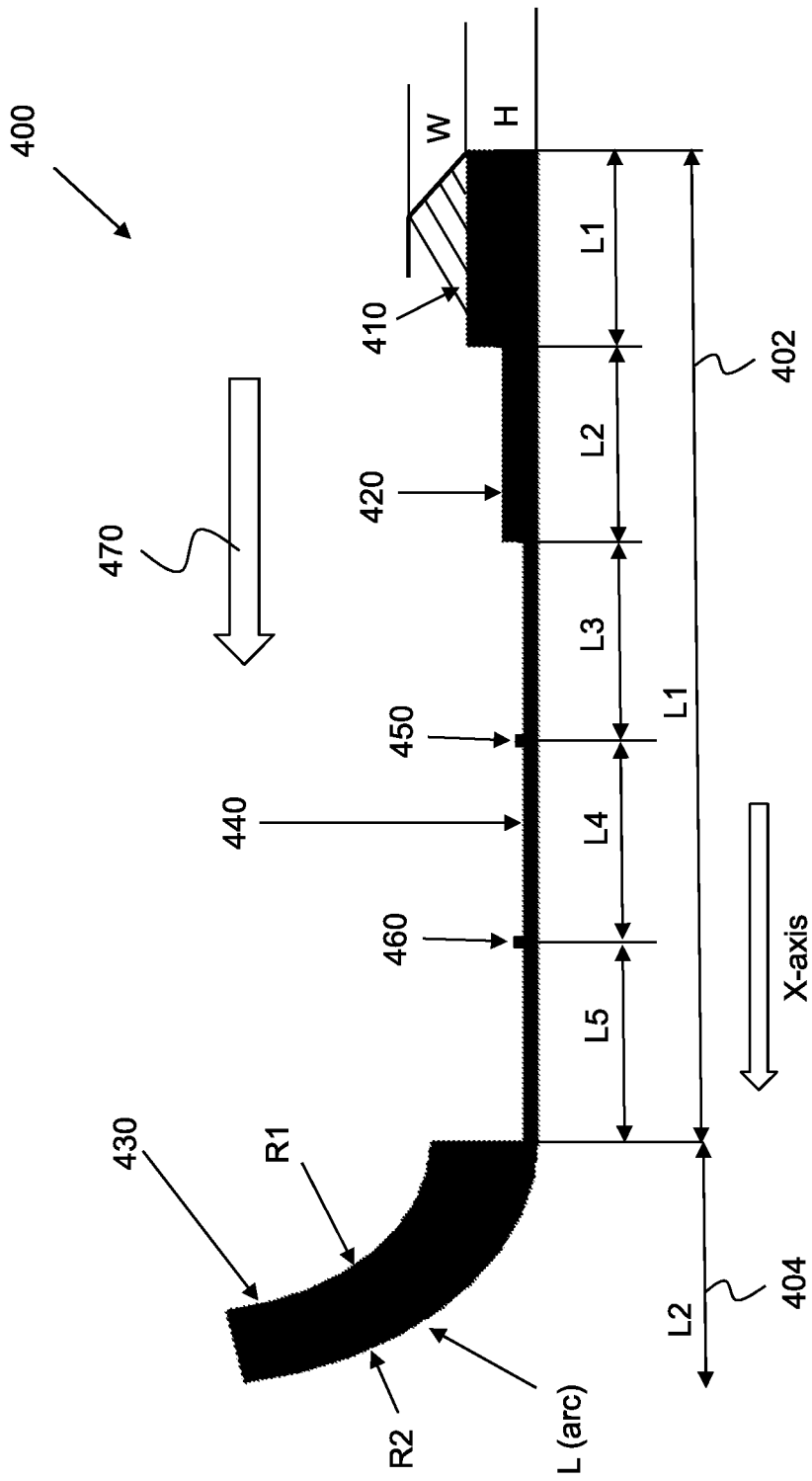
FIG. 4 is a schematic cross-section view of yet another example of an arched LFS, which may be used in-vivo device according to an embodiment of the present invention.

FIG. 4 schematically illustrates a semi- (one-) curved LFS according to another example embodiment. LFS 400 may include a sample pad 410, a conjugate pad 420 and an absorbent pad 430. Between conjugate pad 420 and absorbent pad 430 is located or interposed a cellulose-based membrane 440. Cellulose-based membrane 440 may include a test line 450 and a control line 460.

In the configuration shown in FIG. 4 LFS 400 includes a straight segment (402) and a curved segment (404). The overall length (L01+L02) of LFS 400 may be, for example 25 mm, or about 25 mm (e.g., 25 mm±3 mm). Straight segment 402 may be 20 mm long, or about 20 mm long. Curved segment 404 in a direction 470 coinciding with straight segment 402 lengthwise axis (the projection of absorbent pad 430 onto the X-axis), may be, for example, 5 mm long, or about 5 mm long. The length L1 of sample pad 410, length L2 of conjugate pad 420 and length L(arc) of curved absorbent pad 430 may each have a value in the range of 3 mm-10 mm, for example. (Other length ranges may be used.) By way of example, sample pad 410 and conjugate pad 420 may each be 4 mm long, and the length of the curved absorbent pad 430 (in the 'curving' direction) may be 6 mm long. Test line 450 and control line 460 may divide cellulose membrane 440 to three segments of equal lengths (in FIG. 4 each segment is 4 mm long, though other values may be used). The fluids reaching sample pad 410 move in LFS 400 in direction 470, towards absorbent pad 430 that stores excess fluid. Unlike FIGS. 2 and 3 that show absorbent pads (240, 330) that are straight, FIG. 4 shows an absorbent pad that is curved. The internal radius R1 and external radius R2 of curved absorbent pad 430 may respectively be 3.5 mm and 5 mm.

The thickness of sample pad 410, thickness of conjugate pad 420 and thickness of absorbent pad 430 may each have a value in the range of 0.5 mm-4 mm, for example. (Other thickness ranges may be used.) By way of example, sample pad 410 may have a thickness that is greater than the thickness of conjugate pad 420. Absorbent pad 430 may have a thickness that is greater, the same as or less than the thickness of conjugate pad 420. Absorbent pad 430 may have a thickness that is greater, the same as or less than the thickness of sample pad 410. By way of example, sample pad 410 may be 1 mm thick, conjugate pad 420 may be 0.45 mm thick, and absorbent pad 430 may be 6 mm thick. LFS 400 may have a width (W) in the range of, for example, 3 mm-5 mm (Other width ranges may be used.)

LFS 400 is configured to be accommodated in a swallowable in-vivo device and to function in a similar way as LFS 210 and LFS 300.

Figure 5A:
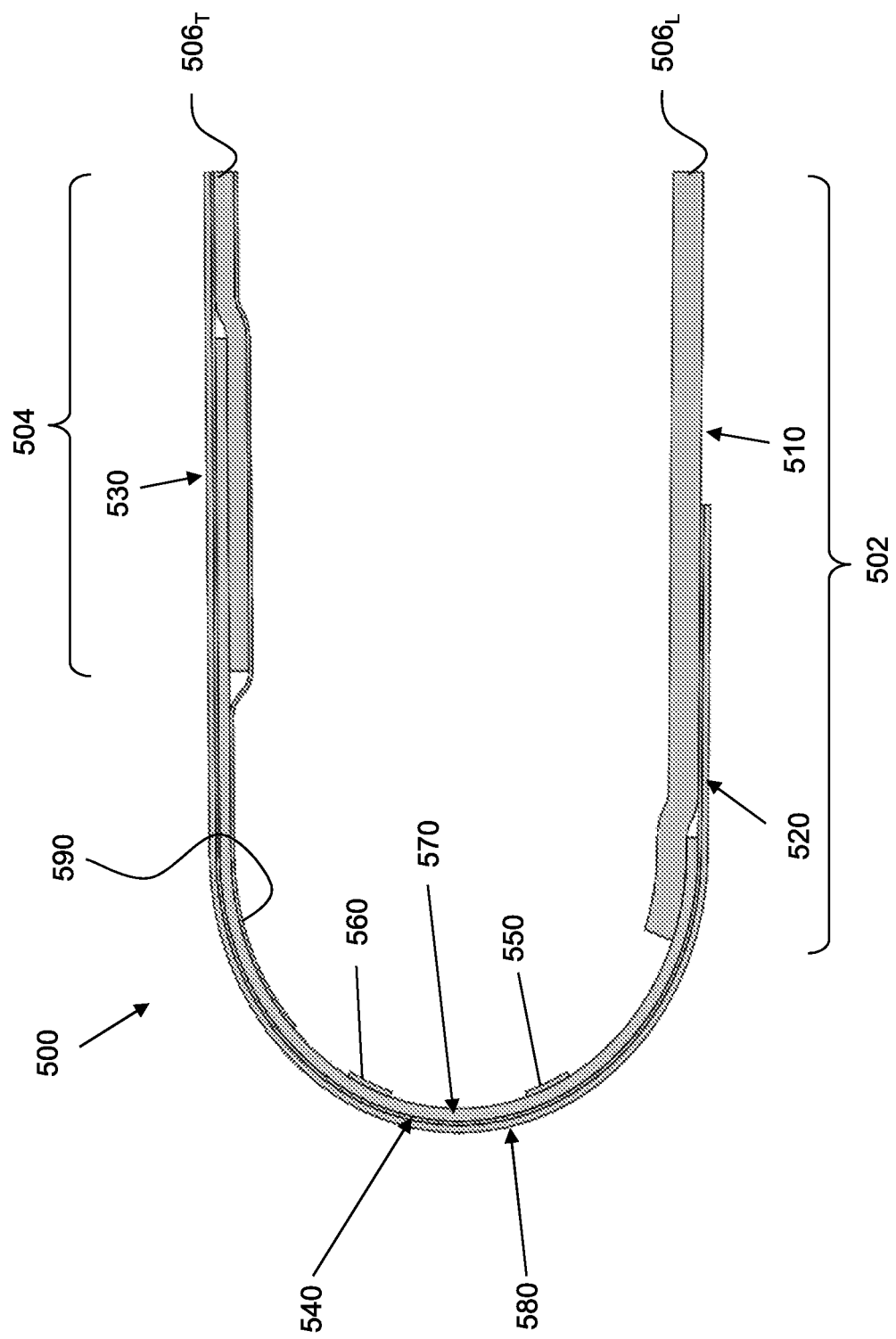
FIG. 5A is a schematic cross-section view of an example of a "U"-shaped LFS, which may be used in an in-vivo device according to an embodiment of the present invention.

FIG. 5 schematically illustrates a "U"-shaped LFS according to an example embodiment. "U"-shaped LFS 500 includes a sample pad 510, a conjugate pad 520, an absorbent pad 530 and a test section 570 that includes a cellulose membrane 540, a test line 550 and a control line 560. Also shown in FIG. 5 are various sizes/lengths/radiuses/angles, etc. of the segments forming LFS 500.

While test section 570 is, or may be or have semicircular, or near semicircular, sample pad 510 and conjugate pad 520 are, or form, or may form a first straight segment or leg (502) of LFS 500, and absorbent pad 530 is or forms, or may be or form a second straight segment or leg (504) of LFS 500, where the two straight segments/legs are, or may be, parallel.

FIG. 6 illustrates a straight LFS according to an example embodiment. LFS 600 includes a sample pad, a conjugate pad, an absorbent pad and a test section 602 that includes a cellulose membrane, a test line and a control line. (FIGS. 7A-7D show three-dimensional views of alternative LFSs structures.)

Figure 8:
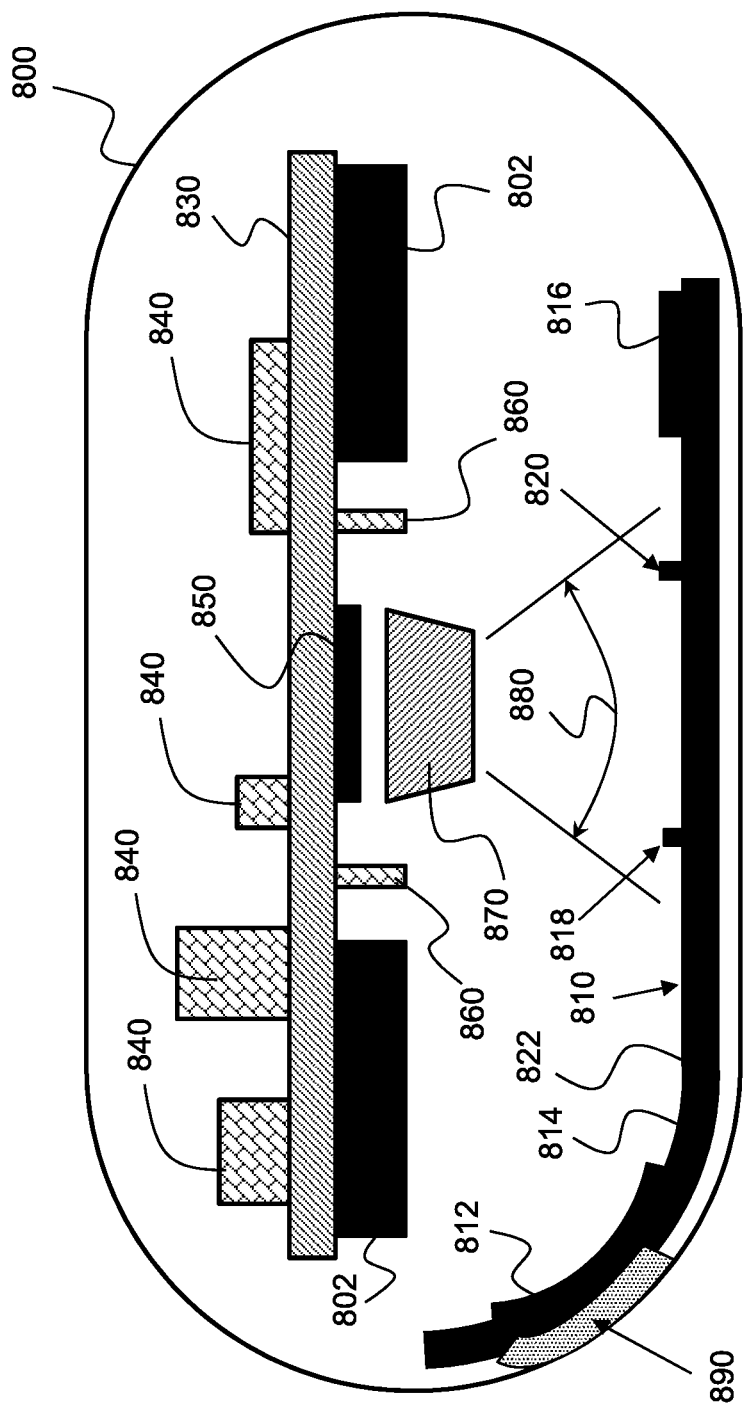
FIG. 8 is a schematic cross-section view of an in-vivo device according to an embodiment of the present invention, containing a LFS.

FIG. 8 schematically illustrates an in-vivo device ("capsule") according to an example embodiment. Capsule 800 may include a LFS 810 and a printed circuit board ("PCB") 830. LFS 810 may include a sample pad 812, a conjugate pad 814, an absorbent pad 816 and a cellulose membrane 822 including a test line 818 and a control line 820.

PCB 830 may include various electrical components 840 (e.g., processor, controller, memory, transmitter, etc.), an image sensor (imager) 850 and illumination source 860. Capsule 800 may also have an optical section 870. Imager 850 and optical section 870 may have a field of view ("FOV") 880 such that imager 850, an example sensor, can take images of (sense) both test line 818 and control line 820 in order to enable, for example the on-board processor or controller, to determine, based on the visual state of the two lines (818, 820), whether the fluids tested by capsule 800 include a sought for fluid particles or substance(s). The controller may use the on-board transmitter to transmit this information, for example, to a remote receiver that may be, for example, a handheld device or a data recorder worn by a subject. Plug 890 may be made of biodegradable material that degrades at an intended (predetermined) site/location in the GI tract.

The LFS shown embedded in FIG. 8 (LFS 810) is semi-curved LFS. However, the LFS to be used by a capsule similar to capsule 800 may have other configurations or structures, for example it may have any of the configurations/structures disclosed in FIGS. 2-7D. Capsule 800 may be powered, for example, by batteries 802.

Figure 9:
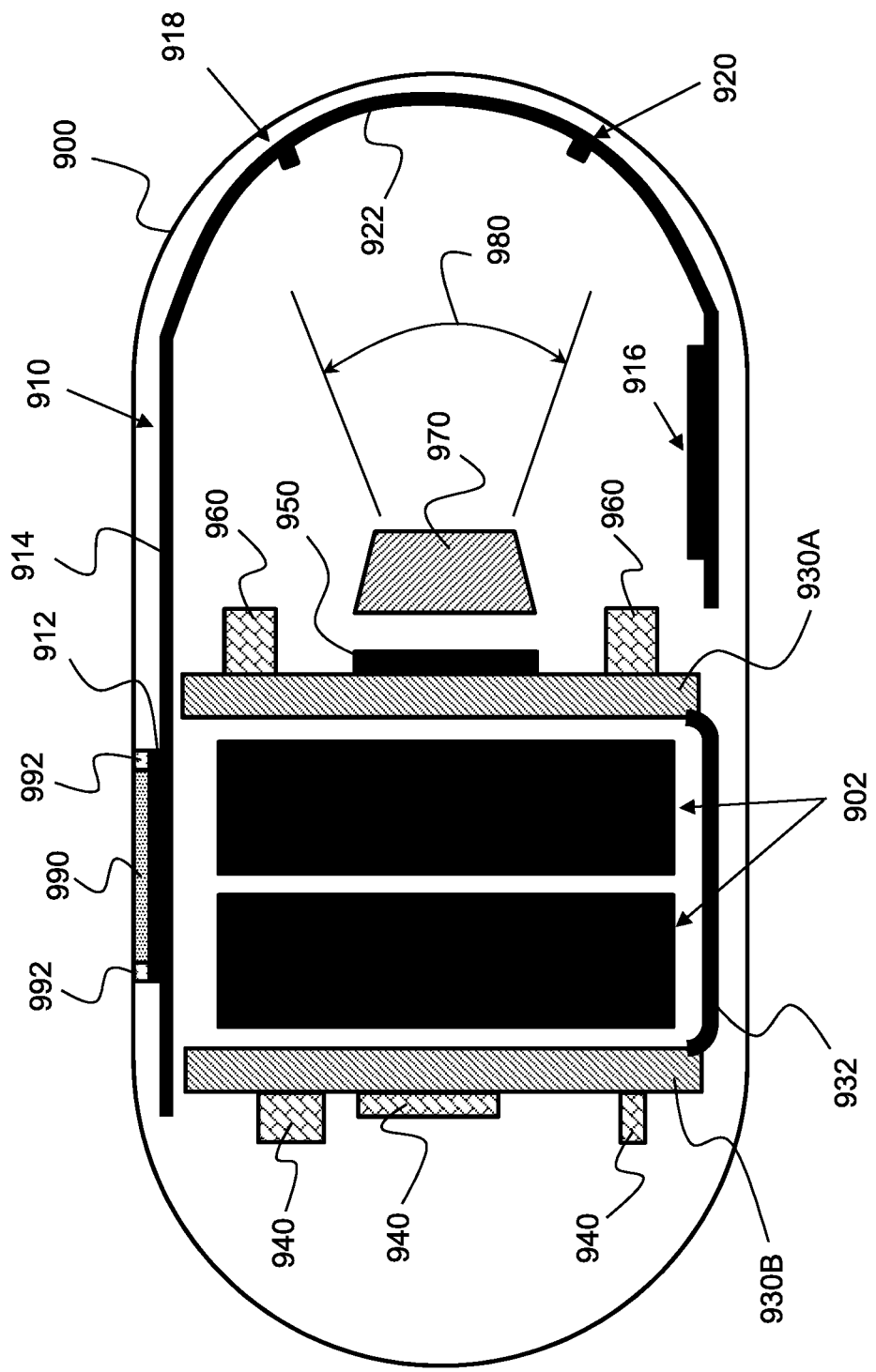
FIG. 9 is a schematic cross-section view of an in-vivo device according to another embodiment of the present invention, containing a LFS.

FIG. 9 schematically illustrates an in-vivo device (capsule) according to another example embodiment. Capsule 900 may include a LFS 910 and a PCB 930. LFS 910 may include a sample pad 912, a conjugate pad 914, an absorbent pad 916 and a cellulose membrane 922 that includes a test line 918 and a control line 920.

PCB 930 may include two PCB portions (930A and 930B) on which various electrical components 940 (e.g., processor, controller, memory, transmitter, etc.) may be mounted/assembled. PCB portions (930A and 930B may be interconnected by a flexible flat cable 932. (PCB 930 may include more than two PCB portions.)

PCB 930 may also include an image sensor (imager) 950 and illumination source 960. Capsule 900 may also have an optical section 970. Imager 950 and optical section 970 may have a field of view (FOV) 980 such that imager 950 can take images of both test line 918 and control line 920, in order to enable, for example the on-board processor or controller, to determine, based on the visual state of the two lines (918, 920), whether the fluids tested by capsule 900 include sought for fluid particles. The controller may use the on-board transmitter to transmit this information, for example, to a remote receiver that may be, for example, a handheld device or a data recorder worn by a subject). Plug 990 may be releasable by being made of biodegradable material that degrades at an intended site in the GI tract. Alternatively, an "O"-ring 992 that secures plug 990 in place on capsule 900 to seal it from external fluids/content, may be made of biodegradable material that degrades at the intended site in the GI tract. That is, when capsule 900 arrives at the site of interest, the biodegradable "O"-ring degrades, and plug 990 is removed to thereby expose LFS 910 to in-situ body fluids. Both O-ring 992 and plug 990 may be made of biodegradable material(s). However, the O-ring may be subjected to more strict requirements because it has to biodegrade at specific GI site (e.g., in response to the chemical and/or bacterial environment), whereas the plug, once removed from capsule 900, can be given more time to disintegrate.

Figure 10A:
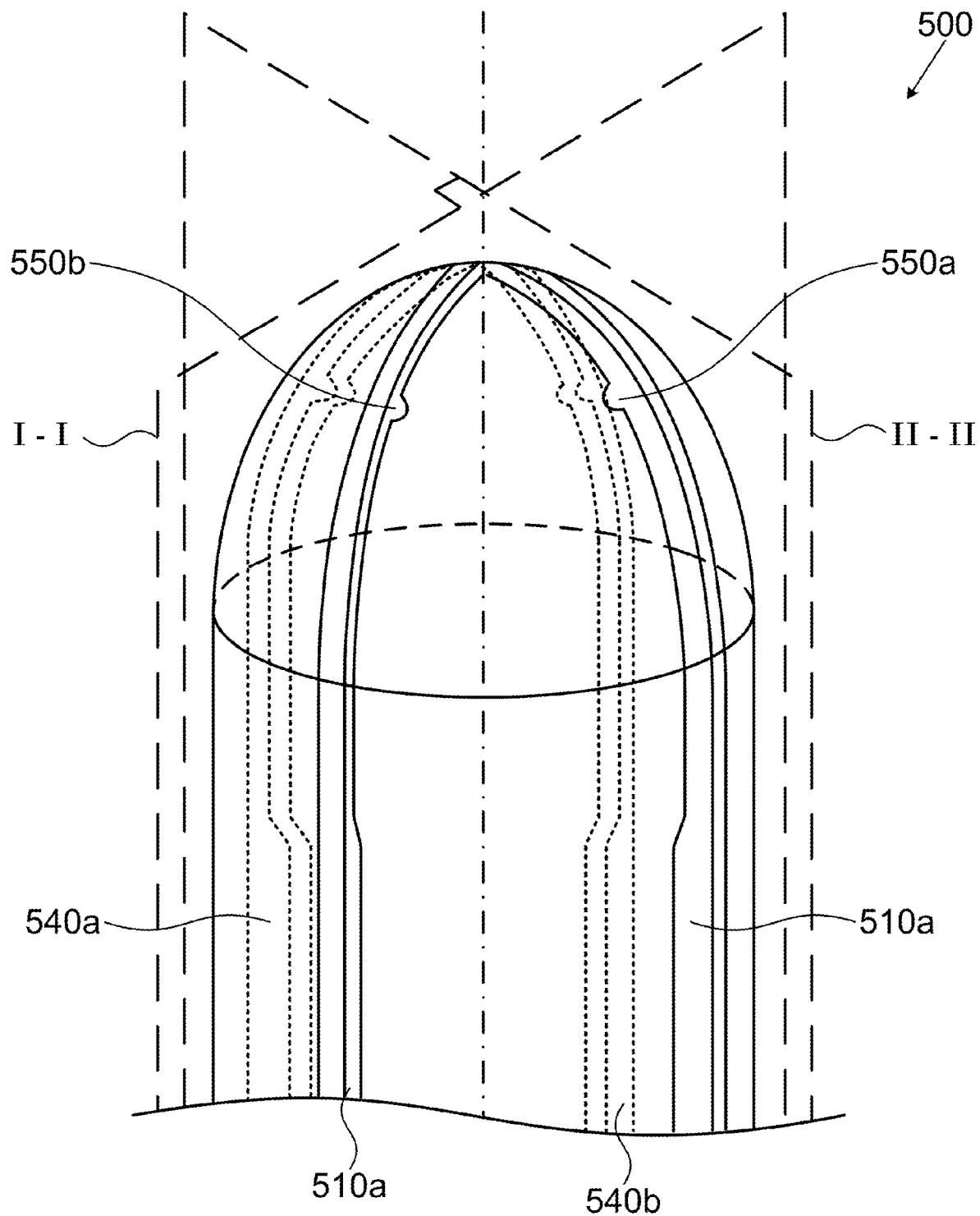
FIG. 10A is a schematic isometric representation of an arrangement of multiple LFSs used in the same in-vivo device according to an embodiment of the present invention.
Figure 10B:
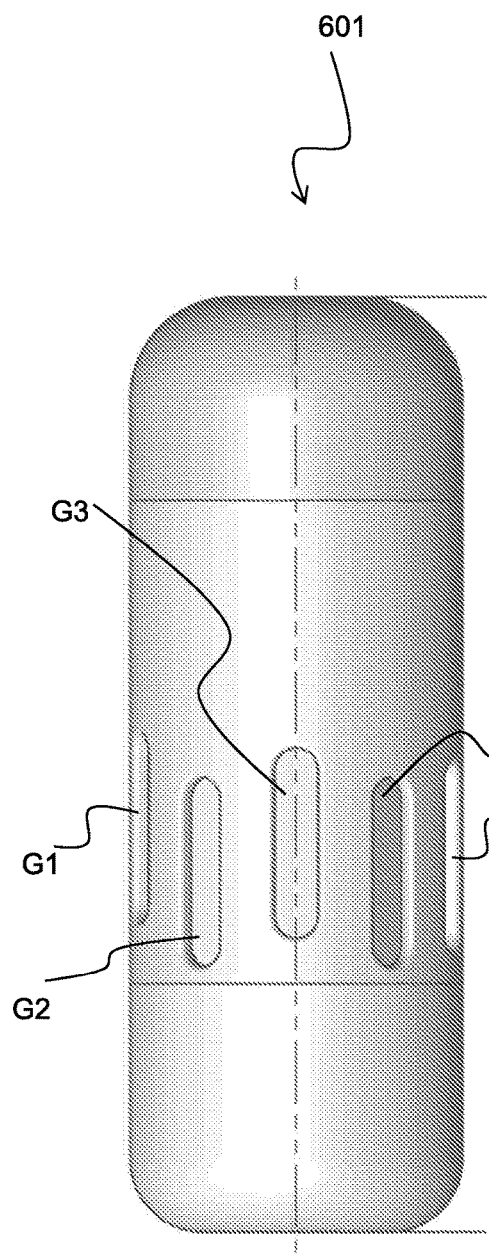
FIGS. 10B and 10C are schematic external and cross-section views, respectively, of an in-vivo device implementing the arrangement shown in FIG. 10A.
Figure 10C:
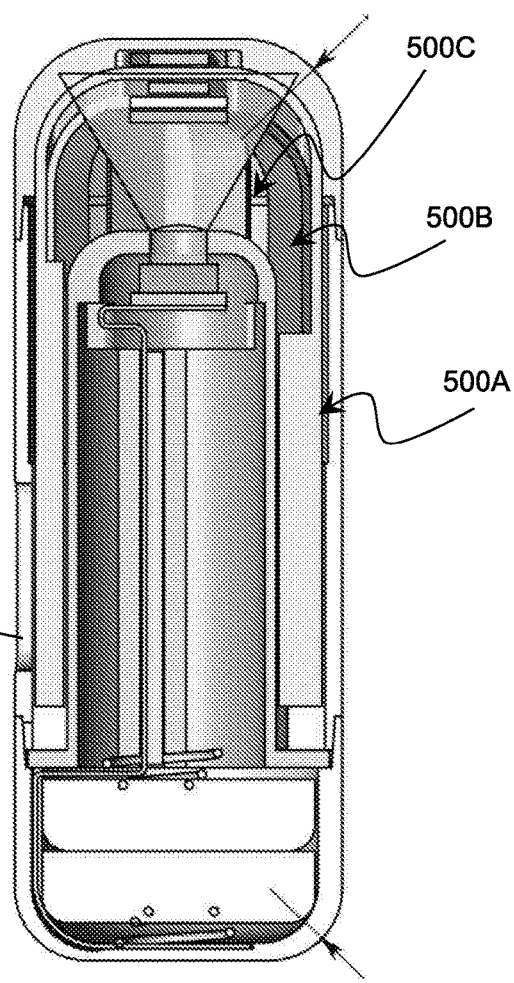

FIG. 10 shows a plug for sealing a gate of, in or on an in-vivo device (e.g., swallowable capsule until the in-vivo device reaches a GI site of interest (e.g., small bowel, colon, a location in the small bowel and/or in the colon, etc.). (The device's gate, through which body fluids are to be drawn into the device's sample pad, is not shown in FIG. 10.) Plug 1000 may have mounted thereon a flat, small, electrode. The in-vivo device may include two sensing electrodes (1010 and 1020) that are in contact with the plug's electrode 1010. Each of sensing electrodes 1010 and 1020 may be connected to a controller 1040 via electrical wires 1500. When 1010 is in place sealing the gate, the electrical resistance that controller 1040 senses between sensing electrodes 1010 and 1020 is very low (e.g., in the order of ohms) because the two sensing electrodes 'close', in this state, an electrical circuit via the plug's electrical electrode 1010. On the other hand, when plug 1000 is removed to open the in-vivo device's gate, the electrical resistance that controller 1040 senses between sensing electrodes 1010 and 1020 is very high (e.g., in the order of mega ohms) because the two sensing electrodes form (at least until body fluids start entering the gate), in this state, an open electrical circuit via the plug's electrical electrode 1010. Controller 1040, which may reside in the in-vivo device, may monitor or measure the electrical resistance between sensing electrodes 1010 and 1020 in order to determine or sense the state of the gate (e.g., "closed" state or "open" state). If controller 1040 determines or senses that the gate is in its "open" state, controller 1040 may use a transmitter in the in-vivo device to transmit this information and, optionally, the time when the plug was removed. As described above, knowing the physical and biological properties of a LFS, the time ("LFS feel time", or "LFT") it takes fluids to fill the LFS and then stop moving may also be known. (Fluids stop moving in the LFS when the absorbent pad's maximum fluid capacity is used to its fullest). Controller 1040 may calculate a time ("fluid flow time", or "FFT") elapsing since the plug is removed, and compare the fluid flow time (FFT) to the LFS feel time (LFT) and, based on the comparison result, controller 1040 may synchronize the timing of the reading of the test line and control line to the LFT.

Plug 1000 may be fully or partly biodegradable, or it may be secured in/on the in-vivo device, to seal the device's gate, by a biodegradable O-ring. In some embodiments both plug and O-ring are biodegradable. Electrical electrode 1010 is made small enough to be easily excreted naturally.

Figure 11A:
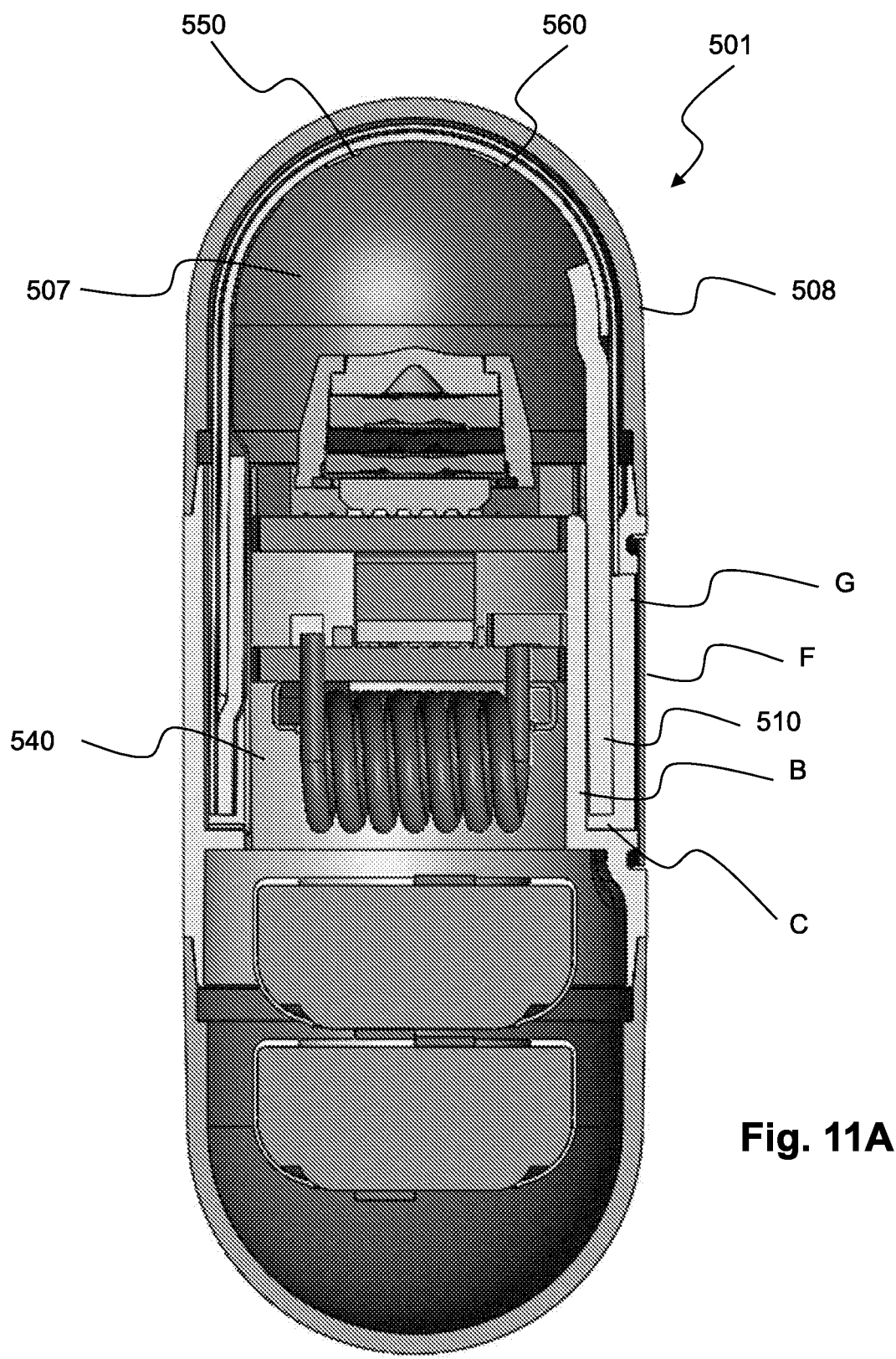
FIG. 11A is a schematic cross-section view of an in-vivo device according to an embodiment of the present invention, containing a LFS, such as the LFS shown in FIGS. 5A and 5B.
Figure 11C:
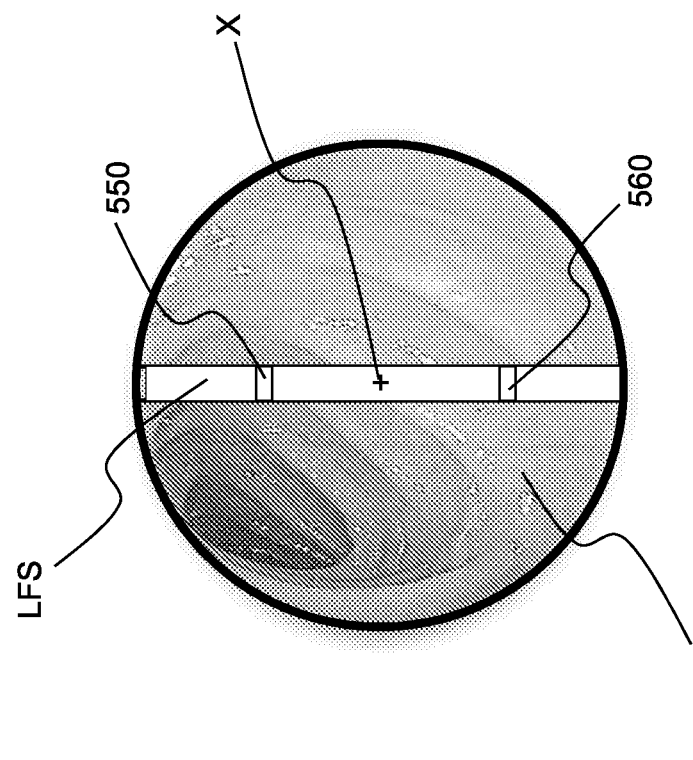
FIG. 11B is a schematic cross-section view of a portion of the in-vivo device shown in FIG. 11A.
Figure 11B:
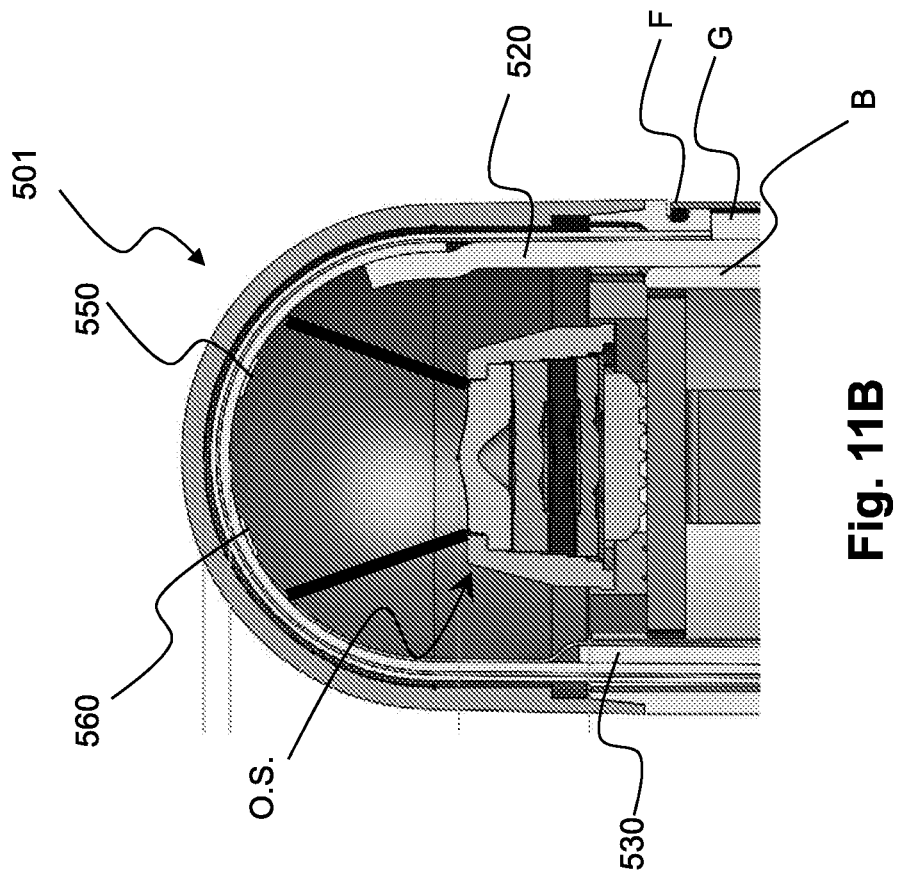

FIG. 11 schematically illustrates a three-dimensional multi-LFS configuration 1100 according to an example embodiment. Multi-LFS configuration 1100 may include two LFSs, which are symbolically shown at 1110 and 1120. Each LFS lying, forming or representing a plan, and the two planes (1112, 1122) respectively formed or represented by LFSs 1110 and 1120 are at (angularly spaced by) angle 1130. Angle 1130 may be, for example, 90 degrees, or about 90 degrees. (Other values may be used for angle 1130.)

A Multi-LFS configuration may include more than two LFSs. For example, a multi-LFS configuration may include three LFSs that may be angularly spaced apart 60 degrees. Each LFS of a multi-LFS configuration (e.g., LFSs 1110 and 1120) may have any of the LFS configurations shown in FIGS. 2-9, and each LFS in each multi-LFS configuration may have a separate controllable gate that may be designed to selectively open (the respective plug may be selectively removed) at preselected GI sites. Depending on the application or implementation, the gates of two or more LFSs may be designed to open at the same GI location in order to enable the in-vivo device to collect more fluids at the same location and of the same type, to thereby corroborate the test results. Gates of some or all of the LFSs may be designed to open at different GI locations in order to enable the in-vivo device to collect fluids at different locations and of the same or different types, to thereby enable the in-vivo device to test GI fluids at multiple locations in the GI tract.

FIG. 12A schematically illustrates a problem that may be caused by an isolator placed in an in-vivo device to isolate a LFS from the electrical components of the in-vivo device. In-vivo device 1200 may include a LFS including a sample pad 1210, a conjugate pad 1220, a cellulose membrane 1230 (with test and control lines), and an absorbent pad 1240. In-vivo device 1200 may include a gate 1250. (Gate 1250 is shown open; that is, without a plug.) In-vivo device 1200 may include a PCB 1260 on which the various electrical components are mounted. (The electrical components are not shown.) In-vivo device 1200 may also include a LFS-PCB interposing, or separation, wall 1270 to physically separate between the LFS and PCB 1260 such that fluids contained in the LFS will not reach/damage PCB 1260. Space constraints require that interposing, or separation, wall 1270 be as close as possible to the LFS. However, the narrower the gap/space 1280 between the two elements, the stronger the capillary effect due to 'stray/parasitic channel' 1290. The capillary force applied by stray/parasitic channel 1290 may cause fluid absorbed by sample pad 1210 to leak (1292) into stray/parasitic channel 1290, which phenomenon may detrimentally affect operation of the LFS as a whole, for example because lesser than sufficient fluid may move in the designated path along the LFS.

FIG. 12B schematically illustrates a solution to the problem described above in connection with FIG. 12A. A fluid redirecting member (FRM) 1212 may be used to redirect 'stray' fluid dripping off the LFS (e.g., from sample pad 1210) back to the LFS (e.g., to conjugate pad 1220). FRM 1212 may be placed in an entrance of parasitic channel 1290 formed by the LFS and the LFS-PCB interposing/separation wall 1270.

Figure 13A:
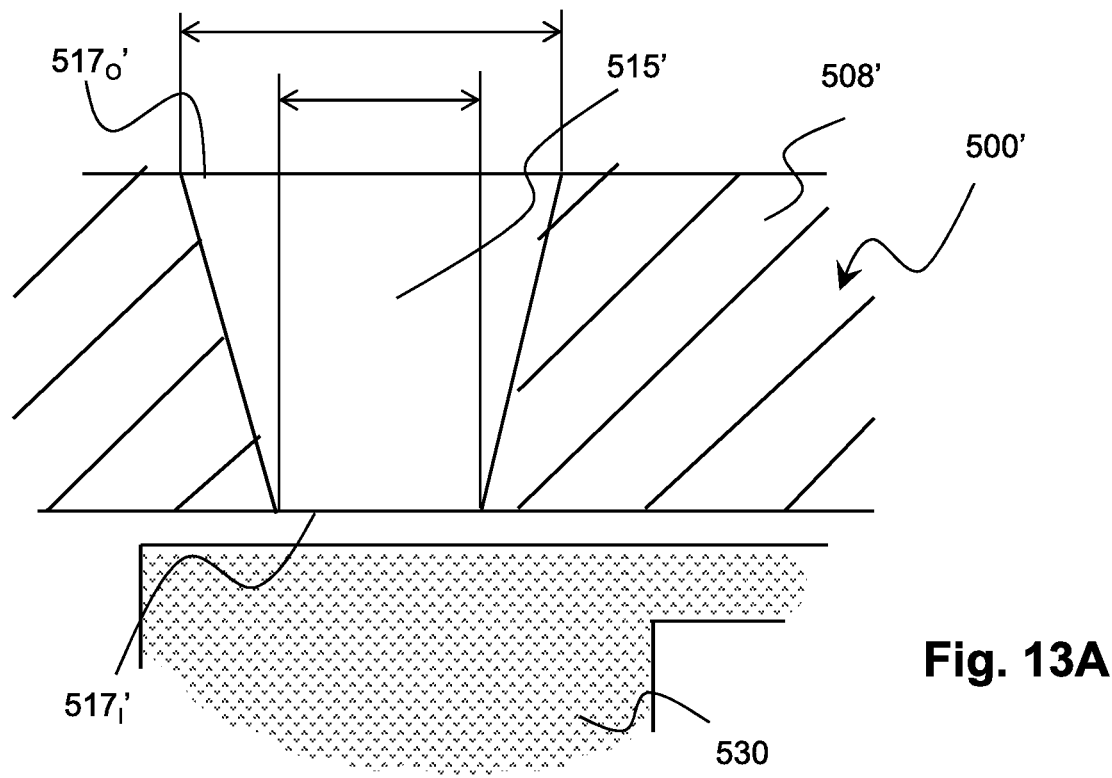
FIGS. 13A and 13B are schematic cross-section views of a portion of the shell wall shown in FIG. 12A, illustrating two different examples of outlet geometry thereof.
Figure 13B:
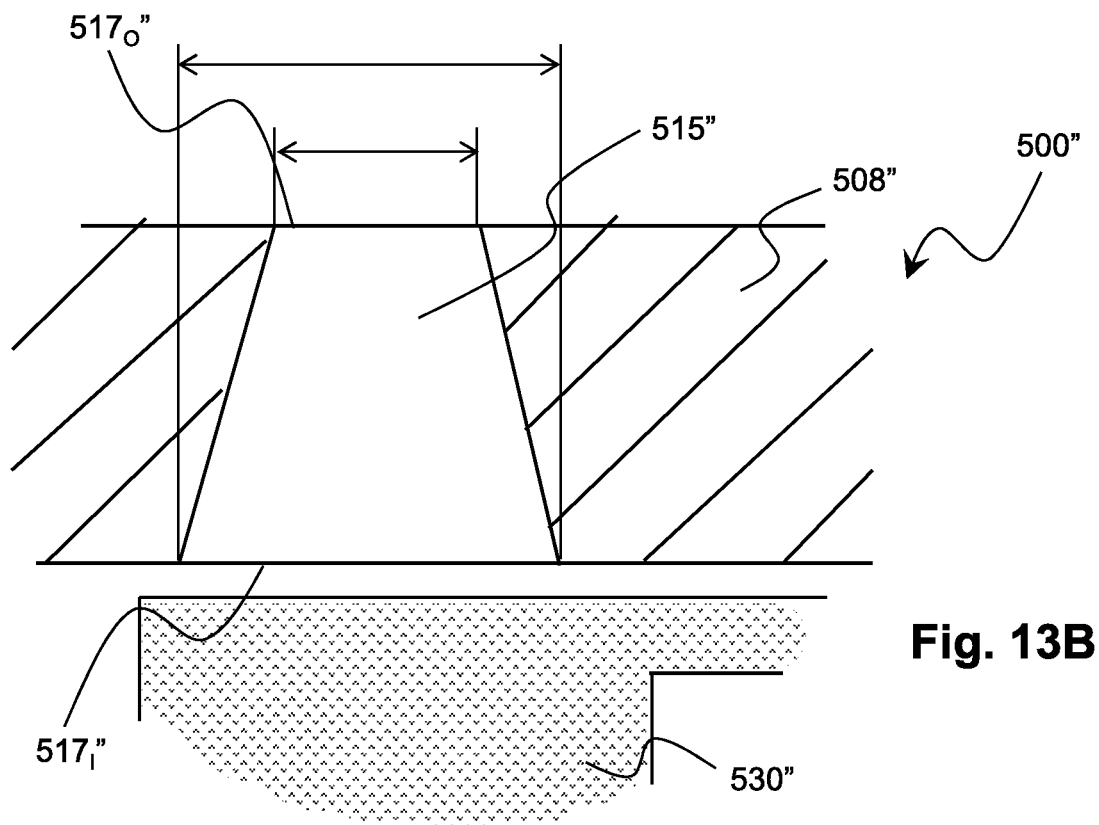
Figure 14A:
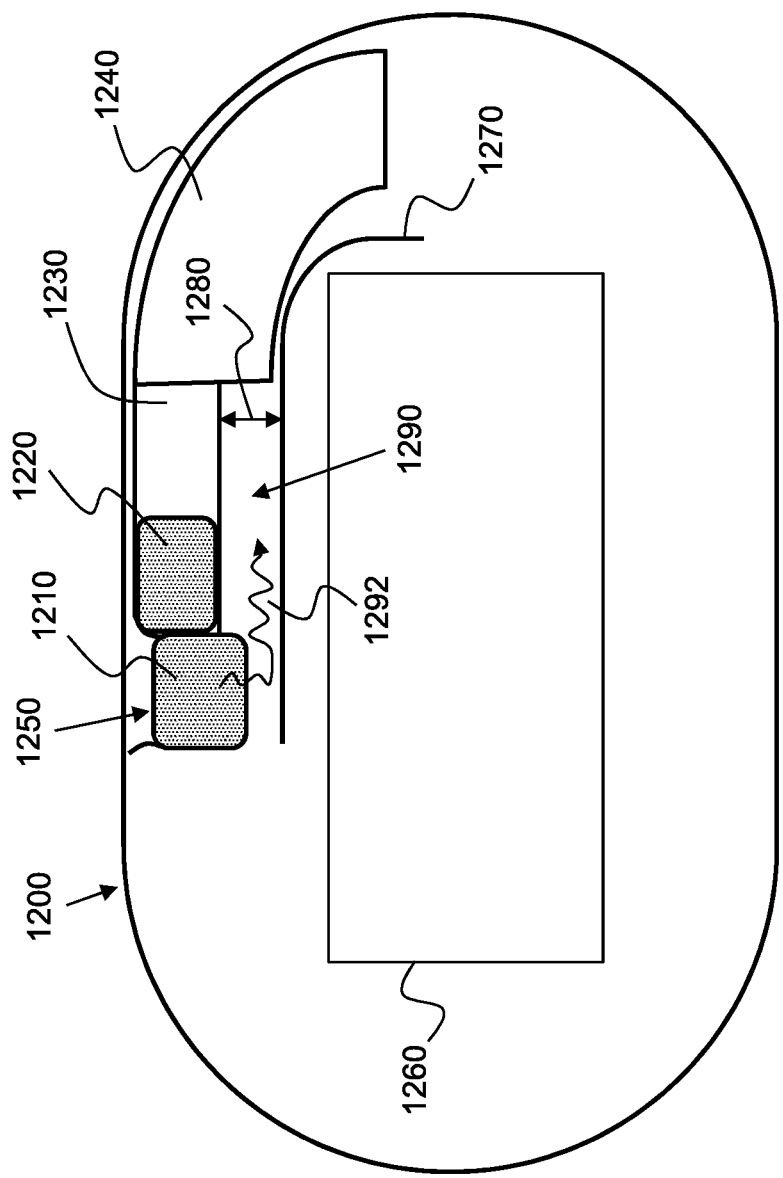
FIG. 14A is a schematic cross-section view of one example of an in-vivo device according to an embodiment of the present invention comprising a parasitic capillary channel.
Figure 14B:
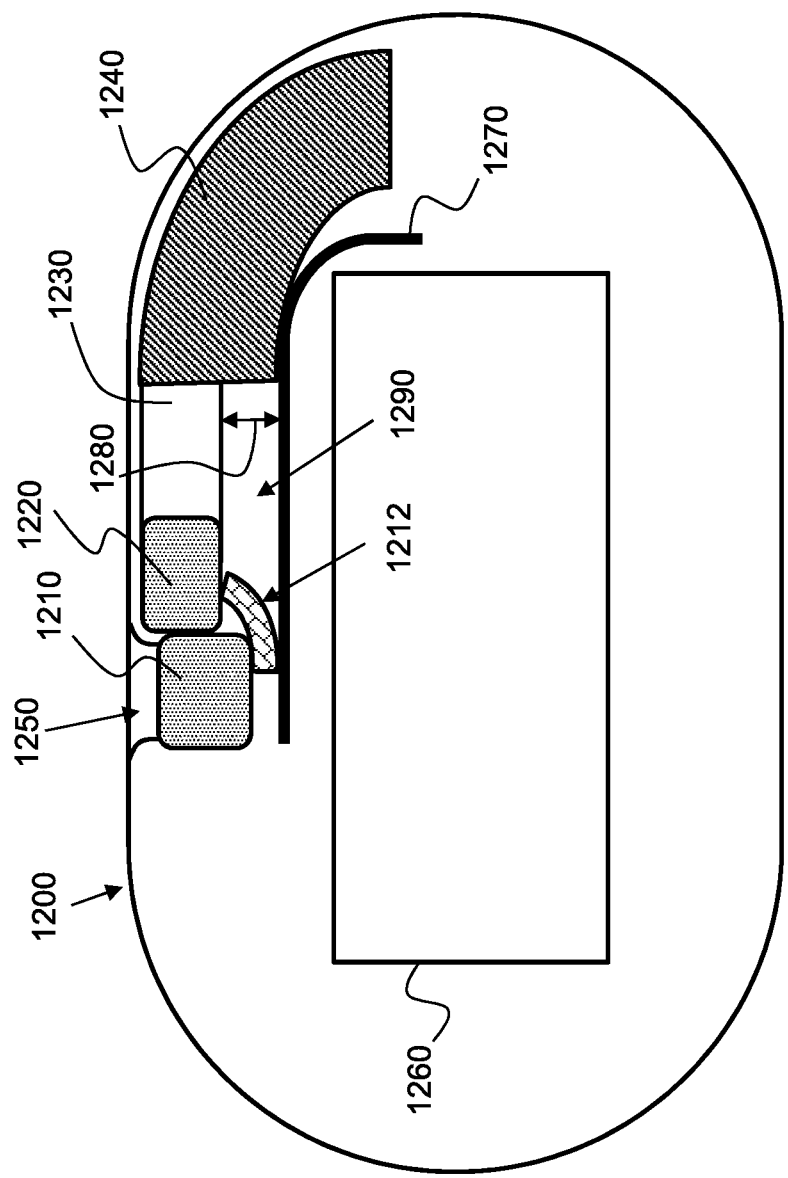
FIG. 14B is a schematic cross-section view of another example of an in-vivo device according to an embodiment of the present invention, comprising a deflector for operating in conjunction with the capillary channel shown in FIG. 14A.
Figure 15:
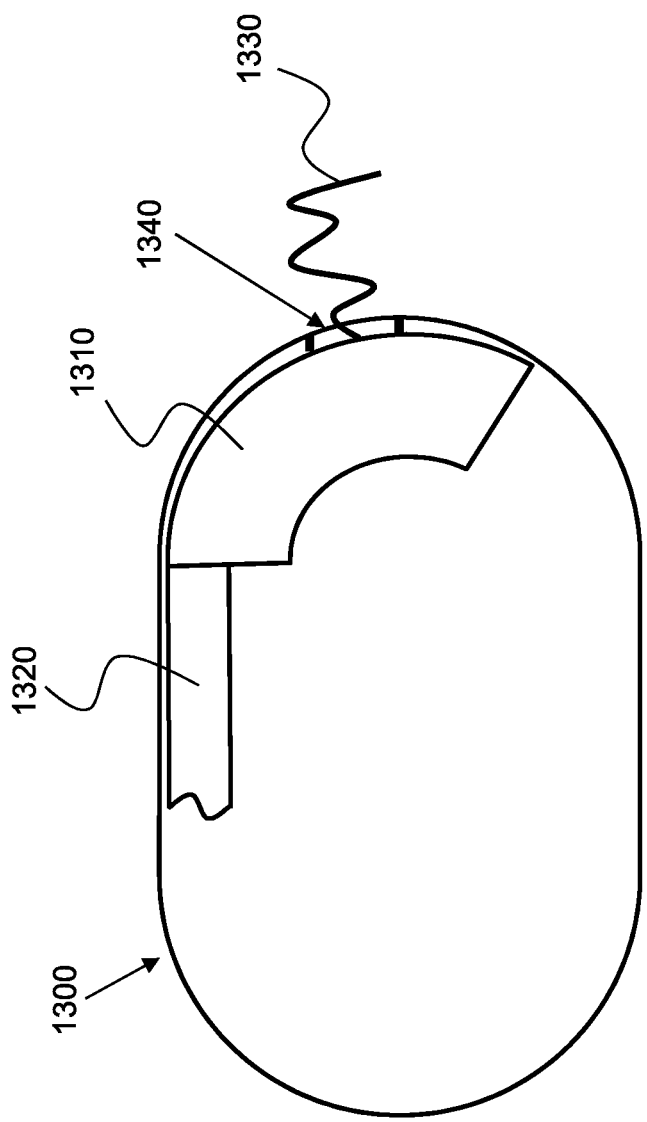
FIG. 15 is a schematic cross-section view of an LFS located in yet another example of an in-vivo device of the present application.
Figure 16:
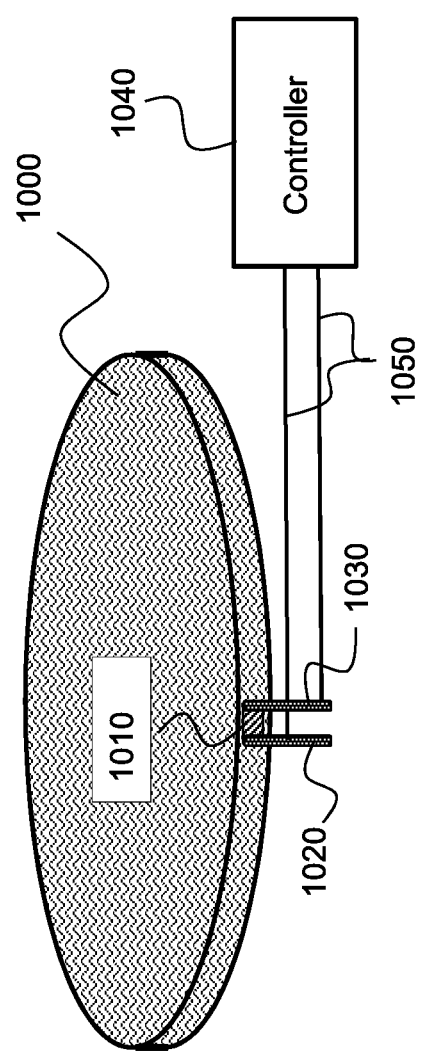
FIG. 16 is a schematic isometric view of a plug for temporarily sealing a gate of the in-vivo device according to an example embodiment.

FIG. 13 schematically illustrates a LFS according to another example embodiment. Only the sample pad (1310) and conjugate pad (1320) of the LFS are shown in FIG. 13 included in an in-vivo device 1300. Sample pad 1310 may include a thread 1330. Thread 1330 may be coiled, or otherwise arranged, inside in-vivo device 1300 when the in-vivo device's gate 1340 is closed. Thread 1330 is shown deployed from in-vivo device 1300 when the in-vivo device's gate 1340 is open. Thread 1330 is a functional extension of sample pad 1310, which is useful in cases where in-vivo device 1300 is to take samples in/from an environment with relatively large amount of material that are 'semi-fluid' or viscous.

Various aspects of the various embodiments disclosed herein are combinable with the other embodiments disclosed herein. Although portions of the discussion herein may relate to chromatography "strips", embodiments of the invention are not limited in this regard, and may include, for example, chromatography units, chromatography elements, chromatography components, chromatography testers, or the like, which may be strip-shaped, non-strip shaped, or may have various suitable shapes and dimensions.

Although portions of the discussion herein may relate to collection and/or release of fluid or body fluid, the present invention is not limited in this regard, and may include, for example, collection and/or release of one or more materials, substances, fluids, solids, gases, materials including both fluids and solids, or the like.

A device, system and method in accordance with some embodiments of the invention may be used, for example, in conjunction with a device which may be inserted into a human body. However, the scope of the present invention is not limited in this regard. For example, some embodiments of the invention may be used in conjunction with a device which may be inserted into a non-human body or an animal body. While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

Those skilled in the art to which this invention pertains will readily appreciate that numerous changes, variations, and modifications can be made without departing from the scope of the invention, mutatis mutandis.

The invention claimed is:

1. A swallowable in-vivo device comprising:
    a shell formed with at least one inlet extending across a shell wall between an inner surface and outer surface thereof, and configured for allowing ingress of fluid at least into said shell, said shell accommodating therein:
    a lateral flow (LF) arrangement configured for absorbing said fluid, said LF arrangement comprising a test zone configured for coming into contact, in-vivo, with a predetermined substance present in said fluid or a compound comprising said substance, thereby causing a change in at least one property of said test zone;
    a sensor configured for sensing, in-vivo, said at least one property, at least when changed by interaction with said fluid;
    wherein said LF arrangement is positioned within the shell such that it has at least one curved segment, and at least one exposure portion spaced from said test zone and juxtaposed with said at least one inlet, configured for absorbing at least some of said fluid passing through said at least one inlet into the shell.

2. A swallowable in-vivo device according to claim 1, wherein said shell comprises a main body extending along a longitudinal axis of the shell and a first end and a second end located on axially opposite sides of said main body, and wherein said curved segment extends transverse to said longitudinal axis.

3. A swallowable in-vivo device according to claim 1, wherein said LF arrangement further comprises a second, longitudinal segment extending generally along the longitudinal axis, and is spaced therefrom.

4. A swallowable in-vivo device according to claim 3, wherein said second, longitudinal segment includes at least a part of said exposure portion.

5. A swallowable in-vivo device according to claim 1, wherein said LF arrangement comprises: a first section comprising a sample zone and a conjugate zone, a second section comprising said test zone, and a third section comprising an absorbent zone.

6. A swallowable in-vivo device according to claim 5, wherein said exposure portion includes at least a part of said sample zone.

7. A swallowable in-vivo device according to claim 5, wherein said curved segment includes at least one of: a part of said second section and a portion of said test zone.

8. A swallowable in-vivo device according to claim 5, wherein said second section is constituted by at least one lateral flow strip (LFS) having formed thereon a test line and a control line.

9. A swallowable in-vivo device according to claim 8, wherein said LFS has a first end and a second and, said curved segment is delimited by a lead end and a trail end, and wherein the LFS assumes any one of the following configurations:
   said lead end constitutes the first end of the LFS and said trail end constitutes the second end of the LFS;
   said lead end constitutes the first end of the LFS and said trail end is spaced from the second end of the LFS;
   said lead end is spaced from the first end of the LFS and said trail end constitutes the second end of the LFS; and
   each of the lead end and the trail end are spaced from each of the first end and second end of the LFS.

10. A swallowable in-vivo device according to claim 8, wherein said LF arrangement comprises two or more LFSs.

11. A swallowable in-vivo device according to claim 10, wherein each of the two or more LFSs defines a virtual plane including the longitudinal axis of the in-vivo device, at least two of such virtual planes being angled to one another about the longitudinal axis.

12. A swallowable in-vivo device according to claim 8, wherein said test line and said control line are diametrically opposed to each other with respect to a longitudinal axis of the shell.

13. A swallowable in-vivo device according to claim 1, wherein said in-vivo device further comprises a gate arrangement juxtaposed with said at least one inlet, and configured for:
   remaining naturally closed, thereby restricting ingress of fluid into said shell through said at least one inlet; and
   opening at least in a predetermined location along the gastrointestinal tract to enable fluid to enter said shell through said at least one inlet to come into contact with said at least one exposure portion.

14. A swallowable in-vivo device according to claim 13, wherein said LF arrangement comprises two or more LFSs, and wherein the in-vivo device comprises two or more gate arrangements, each being associated with a different LFS.

15. A swallowable in-vivo device according to claim 14, wherein the first gate arrangement is configured to open under a first set of conditions while the second gate is configured to open under a second set of conditions different than the first set of conditions.

16. A swallowable in-vivo device according to claim 13, wherein said gate is configured to open under predetermined conditions commensurate to a desired location along the GI tract, thereby exposing said at least one inlet.

17. A swallowable in-vivo device according to claim 16, wherein said conditions are any one of the following types: time dependent conditions, pH dependent conditions, enzymatic environment conditions, prevailing bacteria conditions, temperature conditions and prevailing electromagnetic field conditions.

18. A swallowable in-vivo device according to claim 16, wherein said gate arrangement comprises a closure which is biodegradable and/or dissolvable, subject to the above predetermined conditions, to expose said inlet.

19. A swallowable in-vivo device according to claim 18, wherein said closure is a film layer.

20. A swallowable in-vivo device according to claim 16, wherein said gate comprises a closure and an electrode configured, when the closure is properly positioned with respect to the inlet, for closing an electrical circuit in the in-vivo device, thereby indicating that the inlet is properly sealed.

21. A swallowable in-vivo device according to claim 1, wherein said in-vivo device further comprises:
   a printed circuit board (PCB) on which the sensor and other electrical components are mounted; and
   a separation wall forming a physical barrier between the LF arrangement and the PCB to prevent fluids absorbed by the LF arrangement from reaching the PCB.

22. A swallowable in-vivo device according to claim 1, wherein said shell is further formed with at least one outlet extending across a shell wall between an inner surface and outer surface thereof, said outlet being configured for allowing egress of fluid out of said shell.

23. A swallowable in-vivo device according to claim 1, wherein said LF arrangement has a nominal length L and wherein said at least one inlet and said at least one outlet are located on said shell such that the distance between them is smaller than either of the following: L and the distance between opposite ends of the in-vivo device measured along the longitudinal axis.

* * * * *